US009962259B2

United States Patent
Leo et al.

(10) Patent No.: US 9,962,259 B2
(45) Date of Patent: May 8, 2018

(54) STENT MEMBER, ARTIFICIAL VALVE, AND METHOD OF IMPLANTING THE SAME

(71) Applicants: National University of Singapore, Singapore (SG); Agency for Science, Technology and Research, Singapore (SG)

(72) Inventors: Hwa Liang Leo, Singapore (SG); Kim Fatt Jimmy Hon, Singapore (SG); Fangsen Cui, Singapore (SG); Zhi Wei Chan, Singapore (SG); Gideon Praveen Kumar Vijayakumar, Singapore (SG); Siu Kwan Iris Tan, Singapore (SG); Hui Qun Phang, Singapore (SG)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 181 days.

(21) Appl. No.: 14/890,225

(22) PCT Filed: Jun. 25, 2014

(86) PCT No.: PCT/SG2014/000301
§ 371 (c)(1),
(2) Date: Nov. 10, 2015

(87) PCT Pub. No.: WO2014/209232
PCT Pub. Date: Dec. 31, 2014

(65) Prior Publication Data
US 2016/0081799 A1 Mar. 24, 2016

(30) Foreign Application Priority Data
Jun. 25, 2013 (SG) .............................. 201304925-9

(51) Int. Cl.
*A61F 2/06* (2013.01)
*A61F 2/24* (2006.01)
*A61F 2/848* (2013.01)

(52) U.S. Cl.
CPC ............ *A61F 2/2418* (2013.01); *A61F 2/848* (2013.01); *A61F 2002/8483* (2013.01);
(Continued)

(58) Field of Classification Search
CPC .. A61F 2/24; A61F 2/2418; A61F 2/82; A61F 2/848; A61F 2002/8483;
(Continued)

(56) References Cited

U.S. PATENT DOCUMENTS

| 6,485,496 B1 * | 11/2002 | Suyker | A61B 17/0644 227/901 |
| 7,625,399 B2 * | 12/2009 | Case | A61F 2/2418 623/1.15 |
| 2013/0190861 A1 * | 7/2013 | Chau | A61F 2/2418 623/2.18 |

FOREIGN PATENT DOCUMENTS

EP 2289466 A1 2/2011
WO WO2010121076 A2 10/2010
(Continued)

OTHER PUBLICATIONS

Ma, et al., Double-Crowned Valved Stents for Off-Pump Mitral Valve Replacement, 28 European Journal of Cardio-thoracic Surgery, 194 (2005).
(Continued)

Primary Examiner — Melanie Tyson
(74) Attorney, Agent, or Firm — K. David Crockett, Esq.; Niky Economy Syrengelas, Esq.; Crockett & Crockett, PC

(57) ABSTRACT

In various embodiments, a stent member is provided. The stent member may include a self-expanding stent frame
(Continued)

defining in its expanded position a central annular opening along a longitudinal axis, the opening extending from a first end to a second end of the stent frame. The stent member may include at least one anchoring structure extending radially outwards from the second end of the stent frame. The stent member may further include a biocompatible coating on the stent frame.

15 Claims, 27 Drawing Sheets

(52) U.S. Cl.
CPC ............ *A61F 2210/0014* (2013.01); *A61F 2220/0016* (2013.01); *A61F 2230/0041* (2013.01)

(58) Field of Classification Search
CPC ...... A61F 2002/8486; A61F 2210/0014; A61F 2220/0016; A61F 2310/00389; Y10S 623/90

USPC ..... 623/1.15, 1.18, 1.19, 1.2, 1.24, 1.46, 2.1
See application file for complete search history.

(56) References Cited

FOREIGN PATENT DOCUMENTS

| WO | WO2010121076 A3 | 10/2010 |
| WO | WO2013082454 A1 | 6/2013 |

OTHER PUBLICATIONS

Lozonschi, et al., Transapical Mitral Valved Stent Implantation, 86 The Annals of Thoracic Surgeons, 745 (2008).

* cited by examiner

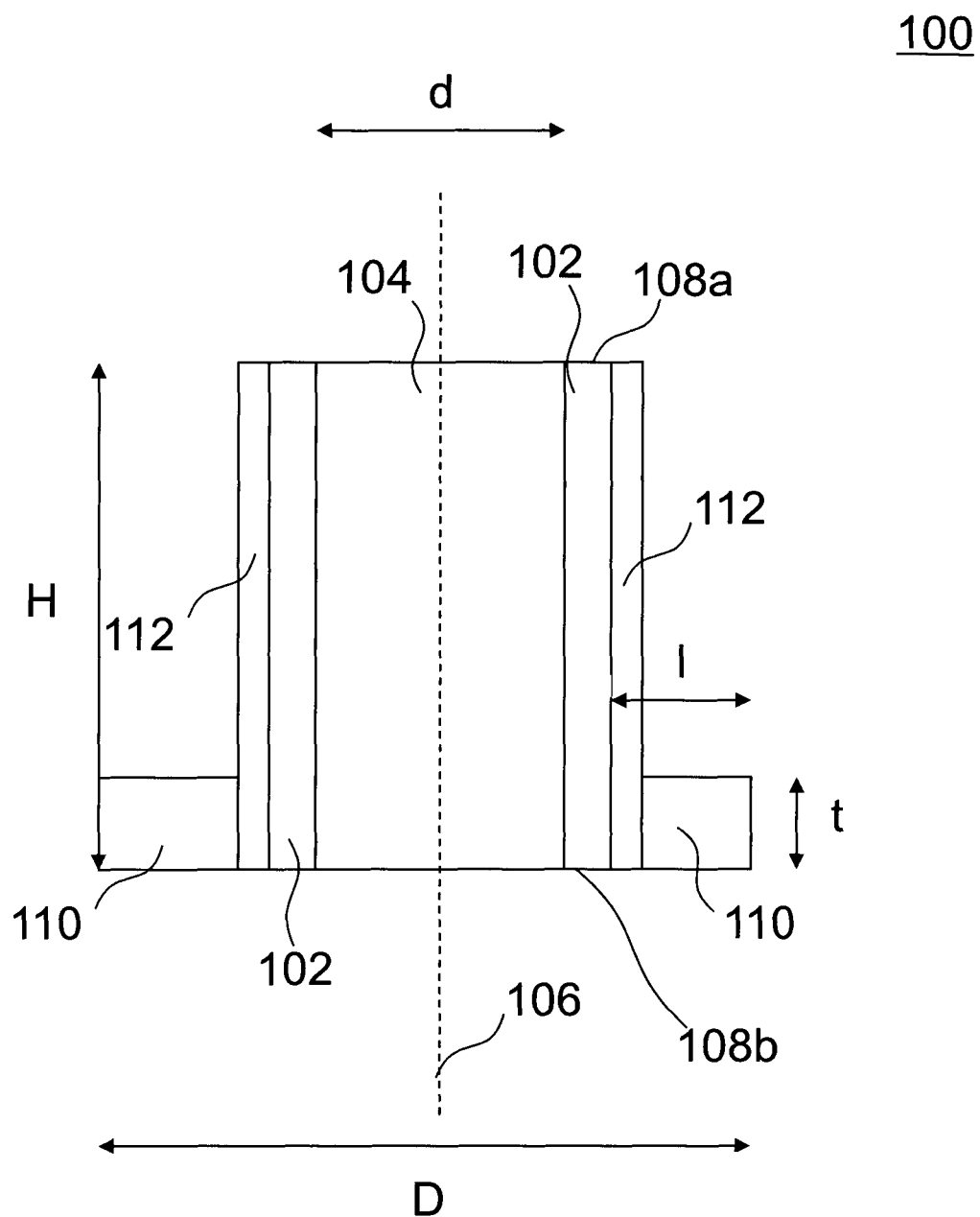

1502: insert the artificial valve using a valve delivery system, the stent member in a collapsed state, wherein the stent member is configured to self-expand to an expanded state upon release by the valve delivery system

STENT MEMBER, ARTIFICIAL VALVE, AND METHOD OF IMPLANTING THE SAME

CROSS-REFERENCE TO RELATED APPLICATIONS

This application claims the benefit of priority of SG application No. 201304925-9 filed Jun. 25, 2013, the contents of it being hereby incorporated by reference in its entirety for all purposes.

TECHNICAL FIELD

Various aspects of this disclosure relate to stent members, artificial valves and methods of implanting the same.

BACKGROUND

Mitral regurgitation (MR) makes up 35% of the observed cases of native valve diseases. The treatment for mitral regurgitation is controversial and depends on the extent of the diseased tissue and the expertise of the surgeon. Even though mitral valve repair is preferable to replacement in many patients because it brings better heart functions with less risk of infection, blood clots and stroke, the surgical procedure may take longer, has steeper learning curve and often requires extensive surgical skill on the part of the surgeon. As a result, only high volume heart centers have the necessary skills to routinely perform mitral valve repairs. Heart valve replacement remains a 'gold standard' in the treatment of many heart valve diseases but suffers from the risks of open chest surgery complications such as infections and blood clot, which could severely compromise the recovery and survival rates of patients.

In summary, for most patients suffering from valvular heart diseases such as mitral regurgitation (MR) and and other heart diseases such as stenosis, heart valve replacement remains the only option for the alleviation of symptoms. However, the surgical approach is associated with substantial operative mortality rates in high risk patients. As a result, a less invasive and a safer approach to heart valve replacements may be required.

SUMMARY

In various embodiments, a stent member is provided. The stent member may include a self-expanding stent frame defining in its expanded position a central annular opening along a longitudinal axis, the opening extending from a first end to a second end of the stent frame. The stent member may include at least one anchoring structure extending radially outwards from the second end of the stent frame. The stent member may further include a biocompatible coating on the stent frame.

BRIEF DESCRIPTION OF THE DRAWINGS

The invention will be better understood with reference to the detailed description when considered in conjunction with the non-limiting examples and the accompanying drawings, in which:

FIG. 1 shows a schematic of a stent member according to various embodiments.

FIG. 15 is a schematic illustrating a method of implanting an artificial valve.

DETAILED DESCRIPTION

Figure 2A:
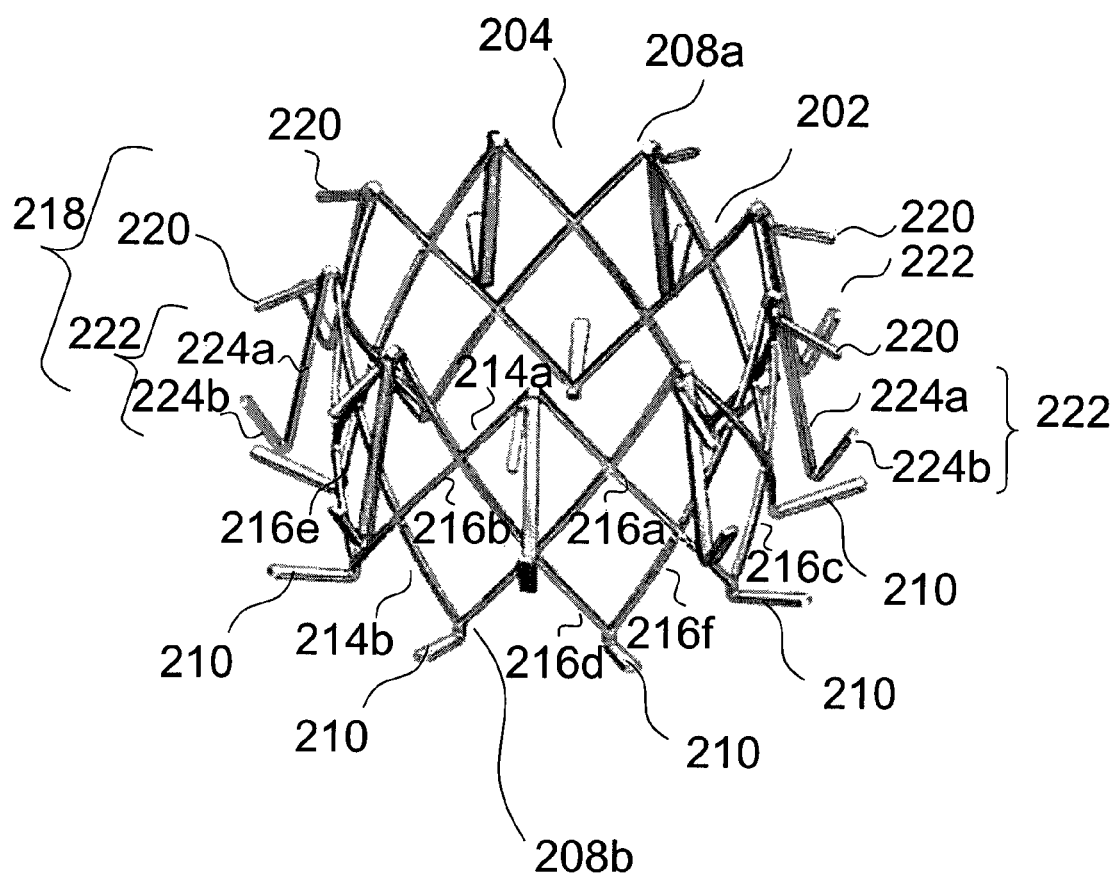
FIG. 2A shows a perspective view of a stent member according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

In order that the invention may be readily understood and put into practical effect, particular embodiments will now be described by way of examples and not limitations, and with reference to the figures.

Features have been labeled wherever appropriate. However, for the sake of clarity and in order to avoid clutter, not all features in some of the figures have been labeled.

It should be understood that the terms "top", "bottom", "upper", "lower", "side" etc., when used in the following description are used for convenience and to aid understanding of relative positions or directions, and not intended to limit the orientation of the stent member or artificial valve, either before or after deployment.

Minimally-invasive replacement of diseased heart valve is an attractive option in addressing the risks of open heart surgery. Percutaneous valve replacement constitutes one of the latest directions in heart valve engineering in which the prosthetic heart valve is delivered and deployed in place of the diseased valve through a delivery device such as a catheter. Currently, there are basically two approaches to the implantation of the valve; 1) transfemorally, via an incision in the femoral vein and transseptally to the valve (as in the mitral valve replacement), and 2) transapical, i.e. via a small incision between the ribs and up through the apex of the heart. This surgical procedure may typically take 1-2 hours (sometime even less) and recovery may be measured in days, not months as in the case of a traditional surgical procedure.

Transcatheter aortic valves currently dominate the research and media communities. Both Edward Life Sciences (Edwards Sapien) and Medtronic, Inc (CoreValve) have established transcatheter programs and have aortic valves already in clinical trials. Edwards Sapien's transcatheter aortic valve has received approval from the United States Food Drug Administration (FDA). The next-generation transcatheter aortic valves currently in clinical trials are Direct Flow Medical, Inc Direct Flow valve, and Sadra Medical, Inc Lotus valve (both are for aortic replacement). Several companies in recent years have also developed their own transcatheter aortic valve programs. These include Heart Leaflet Technologies, Advanced Bioprosthetic Surfaces, Hansen Medical (HNSN) AorTx, JenaValve Technology and the Symetis. None of these aortic valve prostheses are currently in clinical trials. Due to the anatomical and location differences in the aortic and mitral valves, the technical requirements for transcatheter aortic valve may be less demanding than that of the mitral valve. The latter position in the heart may be constrained by relatively restrictive mitral annulus which imposes a strain on the anchoring mechanism design. In contrast, the aortic valve is connected to the aortic arch, which could potentially provide ample space for anchoring of the valve. Indeed, most current transcatheter aortic valve designs (such as CoreValve) may make use of an extended distal frame segment for anchorage.

The advance of transcatheter mitral valve research is generally not as well established as its aortic counterpart. Several conceptual percutaneous mitral valve designs have been proposed and patented, however at present, the documentation on percutaneous replacement of diseased mitral heart valve experiments is still limited. Ma et al. (Eur J Cardiothorac Surg 28(2): 194-8; discussion 198-9) reported in 2005 the first percutaneous mitral valve replacement experiment performed on eight pigs. The percutaneous mitral valve has a shape that resembles a double opposite crown. Two glutaraldehyde preserved aortic and six glutaraldehyde-preserved pulmonary valvular homografts are sutured to the 20 mm diameter Dacron tube, which is attached to the middle stent of the eight valves. The valve prostheses are introduced into the left atrium and deployed at the mitral position. No significant hemodynamic episode was reported 30 mins after stent deployment. The total deployment time took 15-20 s. One animal died of occlusion of the Left Ventricular Outflow Obstruction (LVOT) attributed to the dislodgement of the implant as a result of valve-annulus size mismatch 40 mins after the implantation. The remaining seven survived beyond the 40 mins (survival range 40-180 mins). The study demonstrated the feasibility of the transluminal deployment of mitral valve. Lozonschi et al. (Ann Thorac Surg 86(3): 745-8) reported in 2008 the implantation of the similar mitral valve prototype on 10 pigs through trans-apical insertion. All pigs survived the 60 mins postdeployment with no report of abnormal hemodynamic episode. A year before in 2007, Endovalve, Inc presented their first prototype with small preclinical trial with sheep, however there has not been a follow-up since. The Endovalve percutaneous mitral valve, after deployment, has a gripping mechanism that holds the valve prosthesis in place, and a three-point supporting stmt, which lies across the flow orifice upstream of the leaflets to help maintain the annulus geometry of the valve. However, the strut may hinder the orifice flow and compromise the hemodynamic performance of the valve. Even though early experiences with these valve types, are limited, the initial success with the deployment of these valve prostheses are encouraging, highlighting the fact that transcatheter approach to heart valve replacement is increasingly recognized as a more effective alternative to the more invasive surgical valve replacement. Percutaneous mitral valve prostheses may offer the potential to circumvent many of the problems currently faced by open chest surgery.

FIG. 1 shows a schematic 100 of a stent member according to various embodiments. The stent member may include a self-expanding stent frame 102 defining in its expanded position a central annular opening 104 along a longitudinal axis 106. The annular opening may extend from a first end 108a to a second end 108b of the stent frame 102. The stent member may include at least one anchoring structure 110 extending radially outwards from the second end of the stent frame 102. The stent member may further include a biocompatible coating 112 on the stent frame 102.

In other words, a stent member including a stent frame 102 and at least least one anchoring structure 110 extending from the stent frame 102 may be provided. The anchoring structure 110 may protrude outwards from the stent frame 102. The stent frame 102 may expand by itself in the absence of a restraining force. The stent frame 102 may be tubular (in an expanded state) and may include an opening 104 extending axially, i.e. along axis 106, from a first end 108a of the stent frame 102 to a second end 108b of the stent frame 102. The stent member may further include a biocompatible coating 112 on the stent frame 102.

Various embodiments may hold the promise for less surgical-associated complications, with improved patient's survival rate and shorter recovery time. Various embodiments may present a transcatheter approach to the replacement of diseased heart valves, especially mitral heart valves.

In various embodiments, the stent frame 102 may also be referred to as a band mid section or mid section of the valve prosthesis. The stent frame 102 may be a tubular structure. A valve member such as a porcine or bovine pericardial heart valve may be attached or sutured to the stent frame 102. The anchoring structure 110 may also be referred to as a lower supporting frame. The anchoring structure 110 may also be self-expanding.

The anchoring structure 110 may be configured to expand and anchor on biological tissue such as the inflow or outflow annulus of a mitral valve upon release of the stent member from a catheter.

In various embodiments, the artificial valve (including the stent member and the valve member attached or sutured to the stent frame 102) may be referred to as a percutaneous mitral valve or a percutaneous mitral valve replacement device and be configured to replace at least some functions of a biological human mitral valve. The artificial valve may be configured to be deployed between the left atrium and the left ventricle. The artificial valve may be configured to help restore normal physiological flow of blood from the left atrium to the left ventricle. The stent frame 102 may be configured so that the artificial valve may be re-positionable and retrieveable before final deployment, i.e. before the artificial valve is anchored. The percutaneous mitral valve may have a geometry that conform to the three dimensional saddle shape of the human mitral annulus, and may have an elliptical flow orifice akin to the human mitral valve. In other words, the stent frame 102 may be configured so that when a valve member is attached or sutured to the stent frame 102, the resulting artificial valve has a structure that is similar to the human mitral valve, such as having a three dimensional saddle shape and/or elliptical flow orifice.

In various alternate embodiments, the artificial valve may be configured to be deployed between the right atrium and the right ventricle and be configured to replace at least some functions of the tricuspid valve. In various other embodiments, the artificial valve may be configured to be deployed between the aorta and the left ventricle and be configured to replace at least some functions of the aortic valve. The artificial valve may also be generally referred to as a valve prosthesis.

The stent frame 102 may include a looped arrangement along a circumference of the stent frame 102. The looped arrangement may include a plurality of stent struts. Each stent strut may have a first end joined to a first neighbouring stent strut and a second end joined to a second neighbouring stent strut. Each stent strut may be joined to the first neighbouring stent strut at a first angle (e.g. acute angle or obtuse angle). Further, each stent strut may be joined to the second neighbouring stent strut at a second angle (e.g. acute angle or obtuse angle).

In other words, the loop arrangement may include a plurality of stent struts joined to one another to define a circumference of the stent frame 102 when the stent frame 102 is in an expanded state. The loop arrangement may form a closed zig-zag pattern along the circumference. The loop arrangement may zig-zag in a direction substantially parallel to the longitudinal axis 106.

The stent frame 102 may further include a further looped arrangement along the circumference of the stent frame. The further looped arrangement may include a plurality of further stent struts. Each further stent strut may have a first end joined to a further first neighbouring stent strut and a second end joined to a further second neighbouring stent strut. The looped arrangement and the further looped arrangement may be parallel to each other. The looped arrangement and the further looped arrangement may be at a predetermined distance from each other. The further loop arrangement may include a plurality of further stent struts joined to one another to define a circumference of the stent frame 102 when the stent frame 102 is in an expanded state. The further loop arrangement may also form a closed zig-zag pattern along the circumference. The further loop arrangement may also zig-zag in a direction substantially parallel to the longitudinal axis 106.

The stent struts of the looped arrangement may, be joined to the further stent struts of the further looped arrangement (either directly or indirectly) to form a plurality of cells. Cells may also be referred to as interstices. The cells may be in multiples of three. The stent member may include at least three cells. Increasing the number of struts making up the stent frame 102 may increase the strength of the stent frame. However, a high number of stent struts make also make the stent member less flexible for implantation.

The stent frame 102 may further include axial struts aligned substantially parallel to the longitudinal axis 106 of the stent member 102. The stent struts of the looped arrangement may be joined to the further stent struts of the further looped arrangement via the axial struts to form the plurality of cells. In other words, the stent struts of the looped arrangement may be joined indirectly to the stent struts of the further looped arrangement via the axial struts. In various alternate embodiments, the stent struts of the looped arrangement may be joined directly to the further looped arrangement.

In various embodiments, the stent frame 102 may include at least one further anchoring structure extending radially outwards from the first end 108a of the stent frame 102. The further anchoring structure may be configured to expand and anchor on biological tissue such as the inflow or outflow annulus of a valve such as a mitral valve upon release of the stent member from a catheter. In various embodiments, the anchoring structure 110 may be configured to anchor to the inflow annulus of the valve while the further anchoring structure may be configured to anchor to the outflow annulus of the valve. In various alternate embodiments, the further anchoring structure may be configured to anchor to the inflow annulus of the valve while the anchoring structure 110 may be configured to anchor to the outflow annulus of the valve. The further anchoring structure may be referred to as an upper supporting frame. In various embodiments with only the anchoring structure 110, the anchoring structure may be configured to anchor to either the inflow annulus or outflow annulus of the valve. Various embodiments with anchoring structures at one end and further anchoring structures at the other end of the stent may advantageously prevent migration in both directions, and not just in one direction.

In various embodiments, the stent member may include a plurality of further anchoring structures extending radially outwards from the first end 108a of the stent frame 102. Each further anchoring structure may include an elongated member extending radially outwards. Each further anchoring structure may also extend backwards towards to a plane formed by the second end 108b of the stent member 102.

Each further anchoring structure may further include a hook member, the hook member having a first elongate portion and a second elongate portion. The first elongate portion may extend backwards from the first end 108a of the stent frame 102 towards the plane formed by the second end 108b. The second elongate portion may extend from the first elongate portion radially outwards away from the stent frame 102. An artificial valve including the stent member may be delivered to into a human or animal for operation by a valve delivery system such as a catheter. In various embodiments, the stent member may be hooked (e.g. via the hook member) to the release mechanism of the valve delivery system to allow the ease of valve deployment and improve maneuverability that permits the valve to be re-positionable and retrievable before final deployment.

In various other embodiments, the further anchoring structure may instead be or include a skirt frame. An outer diameter of the further anchoring structure may be greater than an outer diameter of the stent frame 102.

The stent member may include a plurality of anchoring structures 110 extending radially outwards from the second end 108b of the stent frame 102. Each anchoring structure 110 may include an elongated member extending radially outwards. The elongated member may also extend backwards towards to a plane formed by the first end 108a of the stent member. In various alternate embodiments, the elongated member may extend away from the plane formed by the first ends 108a of the stent member. Each anchoring structure 110 may further include a plurality of protrusions extending from the elongated member.

In various other embodiments, the anchoring structure 110 may instead be or include a skirt frame. An outer diameter of the anchoring structure 110 is greater than an outer diameter of the stent frame 102.

In various embodiments, the stent frame 102 may further include anchoring protrusions extending from the stent frame 102.

In various embodiments, the stent member may be collapsible. When the stent member is in the collapsed state, the stent struts and/or the further stent struts may be aligned parallel to the longitudinal axis 106. The diameter of the stent frame 102 when the stent member is in the collapsed state may be smaller than the diameter of the stent frame when the stent member is in the expanded state. The stent member may be configured to be deployed by a catheter in a human or animal body when the stent member is in the collapsed state.

In various embodiments, the stent member may include a shape memory alloy such as nitinol (nickel-titanium alloy). The stent frame 102 may be a nitinol frame. The anchoring structure 110 and/or the further anchoring structure may include nitinol.

The stent frame 102 may be self-expanding due to the shape memory alloy such as nitinol. Shape memory alloys may be deformed at temperatures below a predetermined temperature. The anchoring structure 110 and/or further anchoring structure may be configured to expand upon heating due the property of the shape memory alloy such as nitinol. Upon insertion into the human or animal body, the increase in temperature (due to body temperature) may cause the shape memory alloy to recover its original, undeformed shape, thus causing the stent frame 102 and/or anchoring structures and/or further anchoring structures to self-expand.

In various embodiments, the biocompatible coating 112 may include any of polyethylene terephthalate, silicone, polyurethane, or any other suitable materials. The biocompatible coating may improve sealing and reduce or help address paravalvular leakages. Paravalvular leakage refers to blood flowing through a channel between the structure of the implanted valve and cardiac tissue as a result of a lack of appropriate sealing. The biocompatible coating 112 may alternatively or additionally be coated on the at least one anchoring structure 110 and/or at least one further anchoring structure.

In various embodiments, an artificial valve may be provided. The artificial valve may include a stent member according to various embodiments. The artificial valve may further include a valve member attached or sutured to the stent member. The valve member may include or may be made of porcine or bovine pericardium. Alternatively, the valve member may include or be made of any other suitable biological material or any synthetic material such as a polymer. The valve member may include a plurality of leaflets. The leaflets may permit flow of blood through the artificial valve only in one direction. The valve member may be a tri-leaflet valve. In various embodiments, the valve member may be attached or sutured onto part of the upper supporting frame (for maintenance of sufficient valve profile height) and the stent frame.

The artificial valve may be a mitral valve prosthesis. When the artificial valve is positioned between the left ventricle and the left atrium, the stent frame 102 may occupy the mitral annulus. The stent frame 102 may have an outward radial force sufficient to maintain a predetermined size of the valve and to prevent the collapse of the valve. The anchoring structures and/or further anchoring structures once expanded may serve to anchor the heart valve.

In various embodiments, the anchoring structure 110 may be anchored against the outflow wall (ventricular side of the mitral valve annulus-ring) of the mitral valve, while the further anchoring structure may be anchored against the inflow wall (atrial side of the mitral valve annulus-ring) of the mitral valve. The deployment of the mitral valve prosthesis through a catheter may be such that the upper/lower supporting frame expands and anchors itself against the inflow/outflow wall of the valve. The expansion of the anchoring structure 110 and/or further anchoring structures may be followed by the expansion of the stent frame 102. The stent frame 102 may push the diseased mitral valve against the mitral annulus, and then finally the expansion of the lower/upper supporting frames in the ventricular/atrial anchoring against the outflow/inflow side of the prosthesis. The upper supporting frame or further anchoring structure may extend several millimeters into the atrium and conform to the atrium geometry to provide a more secured anchoring of the valve. In addition, the valve may have elliptical flow orifice and three-dimensional saddle annulus geometry akin to the annulus shape of human mitral valve.

The tips of the anchoring structures 110 and/or further anchoring structures may be attached to the release mechanism of the valve delivery system to allow the ease of valve deployment and improve maneuverability of the valve that permits the valve to be re-positionable and retrievable before final deployment.

In various embodiments, the fully expanded lower frame (ventricular side) or anchoring structure 110 may have a radial length (measured radially from the outer circumference of the stent frame 102 outwards to the radially outermost tip of the anchoring structure 110, denoted in FIG. 1 as l) of less than about 10 mm, which is the approximate distance between the edge of the annulus and the outer diameter of the expanded stent frame 102, and may have a thickness (denoted in FIG. 1 as t) of about 10 mm to avoid obstructing outward flow at the aortic valve.

A stent frame 102 configured for deployment in the mitral valve annulus may have a height (measured parallel to axis 106, denoted in FIG. 1 as H) of any value from about 20 mm to about 25 mm, e.g. 21 mm. The stent frame 102 may have to maintain a profile height necessary for the proper working of the leaflets without occluding the left ventricular outflow tract (LVOT). The stent frame 102 may need to have a sufficient height to allow space for movement of the device within the annulus without being dislodged. On the other hand, the height stent frame 102 may not be too great to cause obstruction to blood flow. During deployment, the device may be shifted further into the atrial side so that less than about 10 mm height of the device may be in the ventricle.

Dimensions of the stent frame are such that they can be used for deployment in other parts of the human or animal body, such as to help replace other valves like the tricuspid valve or the aortic valve. The stent frame 102 may have an axial height (H), measured parallel to the longitudinal axis 106, of any value between about 15 to about 30 mm, e.g. about 20 mm to about 25 mm. The stent frame 102 may have an inner diameter (denoted in FIG. 1 by d) of any value of about 20 to about 40 mm, e.g. about 28 to about 36 mm. The stent member may have a diameter, the diameter extending between radially outermost tips from the stent frame 102 (denoted in FIG. 1 by D), of any value between about 30 to about 50 mm, e.g. between about 40 mm to about 44 mm e,g, about 42 mm. The anchoring structure 110 may have a radial length (l) of any value between about 1 mm to about 20 mm, e.g. between about 1 mm to about 10 mm, e.g. about 10 mm. The anchoring structure 110 may have a thickness (t) of any value between about 1 mm to about 20 mm, e.g. about 5 to about 15 mm, e.g. about 10 mm.

In general, the dimensions of the stent member or artificial valve may be dependent on the location the artificial valve is configured to be implanted at. As highlighted earlier, the stent frame 102 of a mitral valve prosthesis may have an axial height less than the stent frame 102 of an aortic valve prosthesis due to the relative lack of space near the annulus of the biological mitral valve. The dimension of the stent member or artificial valve may also be dependent on the organism the stent member or artificial valve is designed for. In addition, the dimensions of the stent member or artificial valve required may also vary from person to person.

Figure 2B:
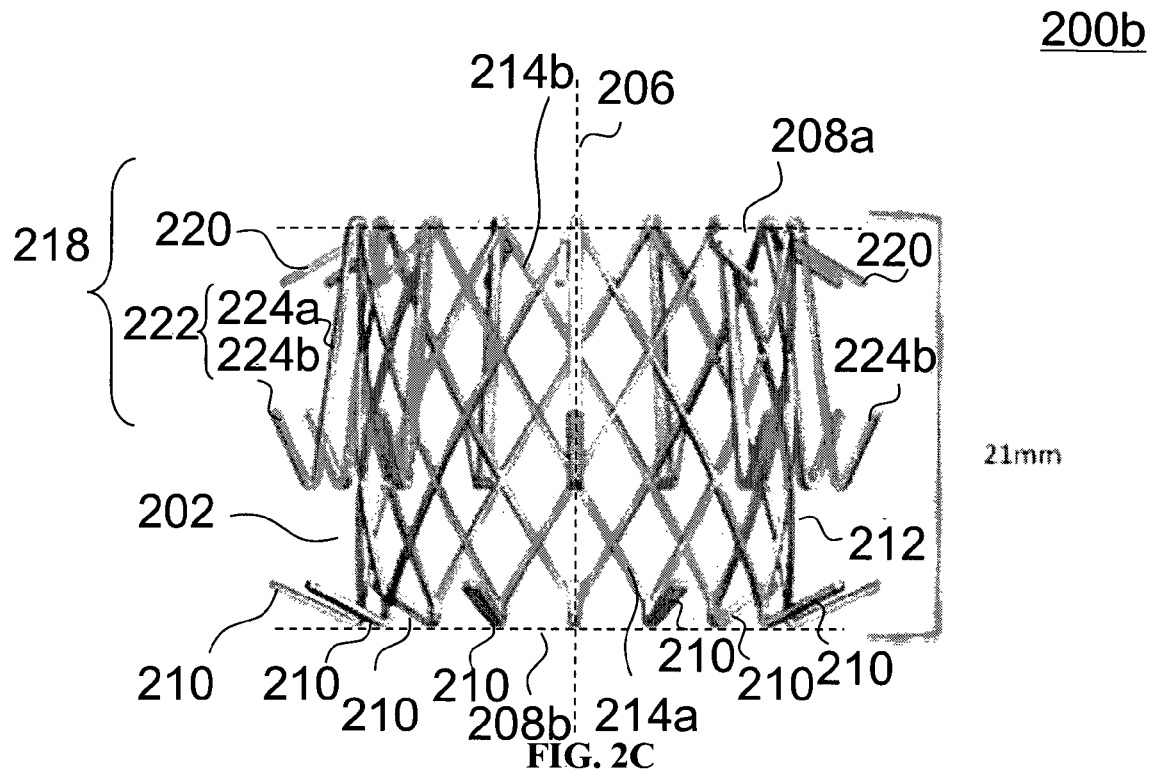
FIG. 2B shows a side view of a stent member similar to the stent member illustrated in FIG. 2A according to various embodiments.
Figure 2C:
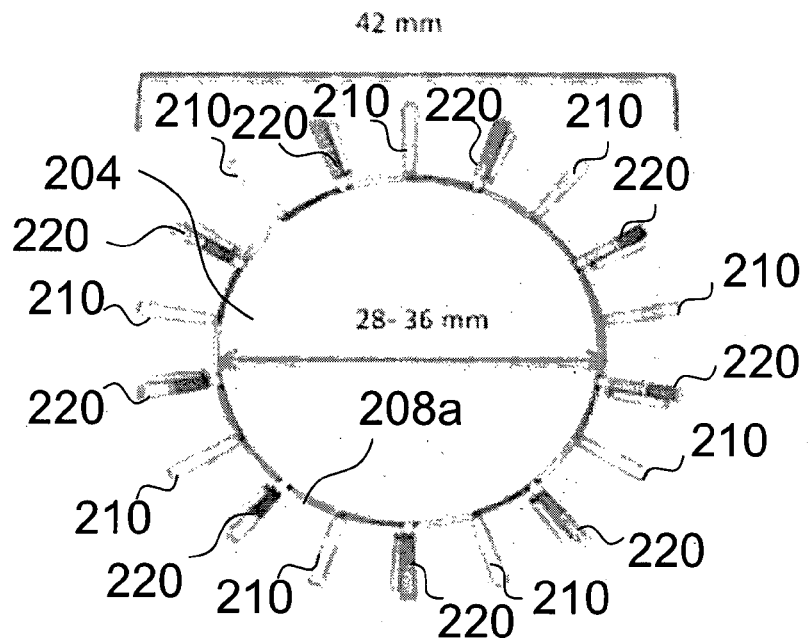
FIG. 2C shows a top view of a stent member similar to the stent member illustrated in FIG. 2A according to various embodiments.

FIG. 2A shows a perspective view 200a of a stent member according to various embodiments. FIG. 2B shows a side view 200b of a stent member similar to the stent member illustrated in FIG. 2A according to various embodiments. FIG. 2C shows a top view 200c of a stent member similar to the stent member illustrated in FIG. 2A according to various embodiments. The stent members shown in FIGS. 2A-C are in the expanded state. A stent member may include a self-expanding stent frame 202 defining in its expanded position a central annular opening 204 along a longitudinal axis 206. The annular opening may extend from a first end 208a to a second end 208b of the stent frame 202. The stent member may include a plurality of anchoring structures 210 extending radially outwards from the second end of the stent frame 202. The stent member may further include a biocompatible coating 212 on the stent frame 202. In other words, the stent frame 202 may be reinforced or insulated with the biocompatible coating 212.

The stent frame 202 may include a looped arrangement 214a along a circumference of the stent frame 202, the looped arrangement 214a including a plurality of stent struts, e.g. 216a, 216b, 216c, each stent strut having a first end joined to a first neighbouring stent strut and a second end joined to a second neighbouring stent strut. For instance, stent strut 216a may have a first end joined to a first neighbouring stent strut 216b and a second end joined to a second neighbouring stent strut 216c. Each stent strut may be joined to the first neighbouring stent strut at a first acute angle, and each stent strut may be joined to the second neighbouring stent strut at a second acute angle. For instance, stent strut 216a may be joined to the first neighbouring stent strut 216b at a first acute angle to form a top crown. Stent strut 216a may be joined to the second neighbouring stent strut 216c to form a bottom crown. The first acute angle may be the same as the second acute angle. The loop arrangement 214a may include a plurality of stent struts joined to one another to define a circumference of the stent frame 202. As shown in FIGS. 2A and 2B, the loop arrangement 214a may form a closed zig-zag pattern along the circumference.

The stent frame may also include a further looped arrangement 214b along the circumference of the stent frame 202. The further looped arrangement 214b may include a plurality of further stent struts 216d, 216e, 216f. Each further stent strut having a first end joined to a further first neighbouring stent strut and a second end joined to a further second neighbouring stent strut. For instance, further stent strut 216d may have a first end joined to a further first neighbouring stent strut 216e and a second end joined to a further second neighbouring stent strut 216f. Each further stent strut may be joined to the further first neighbouring stent strut at a first acute angle, and each stent strut may be joined to the further second neighbouring stent strut at a second acute angle. Similarly, the further stent strut 216d may be joined to the further first neighbouring stent strut 216e to form a top crown and the further stent strut 216d may be joined to the further second neighbouring stent strut 216f to form a bottom crown. The further loop arrangement 214b may include a plurality of further stent struts joined to one another to define a circumference of the stent frame 202. As shown in FIGS. 2A and 2B, the further loop arrangement 214b may form a closed zig-zag pattern along the circumference similar to that for the looped arrangement 214a.

The stent struts of the looped arrangement 214a may be joined directly to the further stent struts of the further looped arrangement 214b to form a plurality of cells or interstices.

The stent frame may further include additional looped arrangements. The stent frame in FIG. 2A includes two looped arrangements 214a, 214b while the stent frame in FIG. 2B includes additional looped arrangements.

A plurality of top crowns may form the first end 208a. A plurality of bottom crowns may form the second end 208b. As shown in FIG. 2A, the stent frame 202 may have 9 top crowns and 9 bottom crowns. A valve member may be attached or sutured on the top crowns. The valve member may additionally or alternatively be attached or sutured on the stent frame 202.

Each anchoring structure 210 may be or may include an individual strut extending or originating from each bottom crown. As seen in FIG. 2A, each anchoring structure 210 may extend or originate from the second end 208b (distal end) radially outwards and backwards towards a plane formed by the first end 208a of the stent frame 202. The anchoring structures 210 may form a conical structure. The anchoring structures 210 may be coated with a biocompatible material.

The stent member may further include a plurality of further anchoring structures 218 extending radially outwards from the first end 208a (proximal end) of the stent frame 202. Each further anchoring structure may include an elongated member or strut 220 extending radially outwards and backwards in a direction towards a plane formed by the second end 208b of the stent member 202. The elongated member or strut 220 may form an acute angle with the stent frame 202.

Each further anchoring structure 218 may alternatively or additionally include a hook member 222. The hook member 222 may include a first elongate portion 224a and a second elongate portion 224b. The first elongate portion 224a may extend backwards from the first end 208a of the stent frame 202 in a direction towards the plane formed by the second end 208b. The second elongate portion 224b may extend from the first elongate portion 224a in a direction outwards away from the stent frame 202. The first elongate portion 224a may form an acute angle with the stent frame 202. The acute angle formed by the first elongate portion 224a with the stent frame may be smaller than the acute angle formed by the elongated member or strut 220 with the stent frame 202 so that the first elongate portion 224a bend backwards closer to the body of the stent frame 202 compared to the elongated member or strut 220. The elongated member or strut 220 may form a pincer with the second elongate portion 224b as shown in FIGS. 2A and 2B. The further anchoring structures 218 may be coated with a biocompatible material.

As shown in FIGS. 2A-C, the anchoring structures 210 and further anchoring structures 218 of a stent member in an expanded state may form cone structures which help to reduce or prevent paravalvular leakages between the mitral annulus and the device. In other words, flow of fluids outside the circumference of the stent frame 202 when the stent member is implanted in a human or animal body may be reduced by the design of the anchoring structures 210, 218 as well as the biocompatible material.

For a typical percutaneous mitral valve replacement device in an expanded state, the diameter of the opening 204 may typically in the range of about 28 mm to about 36 mm, depending on the mitral annulus diameter of the patient. The stent member may have a diameter (the distance extending between radially outermost tips of the anchoring structures or further anchoring structures) of about 42 mm. The stent member may have a height, measured parallel to the longitudinal axis 206, of about 21 mm. However, the dimensions indicated in FIGS. 2B and 2C are not intended to be limiting and the stent member may be of any suitable dimensions.

Figure 2D:
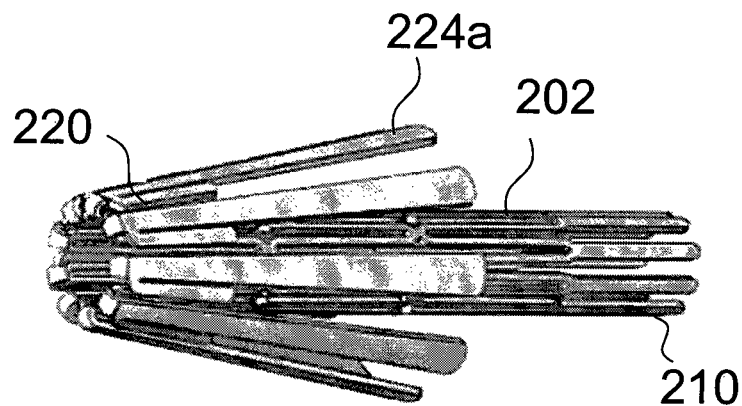
FIG. 2D shows a perspective view of a stent member similar to the stent member illustrated in FIG. 2A in a collapsed state according to various embodiments.

FIG. 2D shows a perspective view 200d of a stent member similar to the stent member illustrated in FIG. 2A in a collapsed state according to various embodiments. When the stent member is in the collapsed state, the stent struts and/or the further stent struts may be aligned parallel to the longitudinal axis 206. The diameter of the stent frame 202 when the stent member is in the collapsed state may be smaller than the diameter of the stent frame when the stent member is in the expanded state. The angles formed by the anchoring structures 210 and/or further anchoring structures 218 with the stent frame 202 may be smaller so that the diameters measured between the outermost tips of the anchoring structures 210 or further anchoring structures (from the stent frame 202) may be smaller compared to when the stent member is in the expanded state. The stent member may be configured to be deployed by a catheter in a human or animal body when the stent member is in the collapsed state.

Figure 2E:
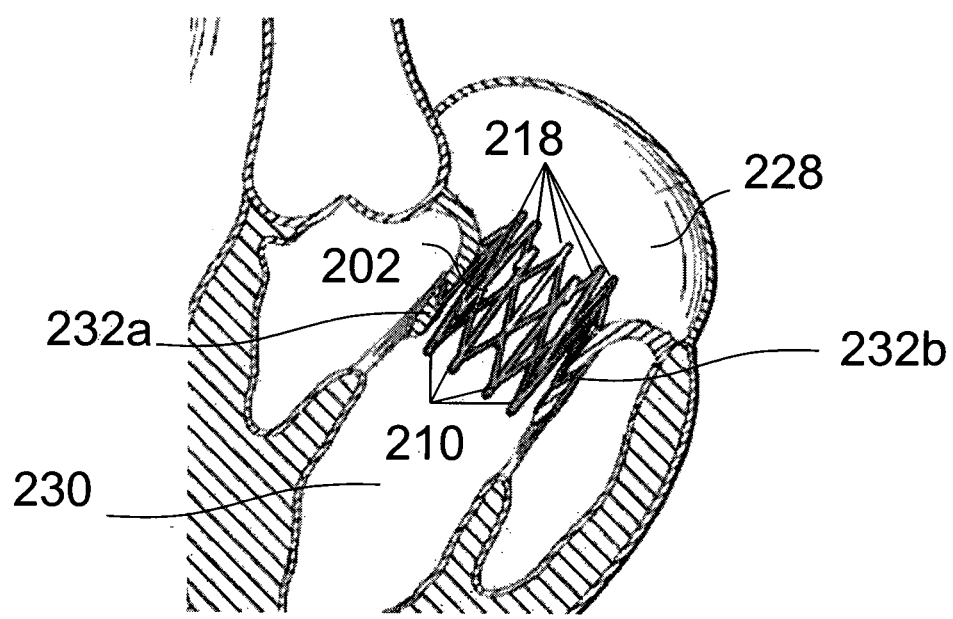
FIG. 2E shows a side view of a stent member similar to the stent member illustrated in FIG. 2A according to various embodiments being deployed as part of a percutaneous mitral valve replacement device in the heart.

FIG. 2E shows a side view 200e of a stent member similar to the stent member illustrated in FIG. 2A according to various embodiments being deployed as part of a percutaneous mitral valve replacement device in the heart. The percutaneous mitral valve replacement device may further include a valve member (not shown in FIG. 2E) attached or sutured to the stent member. As shown in FIG. 2E, the stent member may be positioned between the left atrium 228 and the left ventricle 230. The first end 208a of the stent member may be positioned within the left atrium 228 and the second end 208b of the stent member may be positioned within the left ventricle 230. The self-expanding stent frame 202 may push against the leaflets of the biological mitral valve. The anchoring structures 210 may engage the end portions of the leaflets while the further anchoring structures 218 may engage portions of the left atrium 228. The further anchoring structures 218 may extend several millimeters into the left atrium and may be designed to conform to the atrium geometry for more secure anchoring.

Figure 3A:
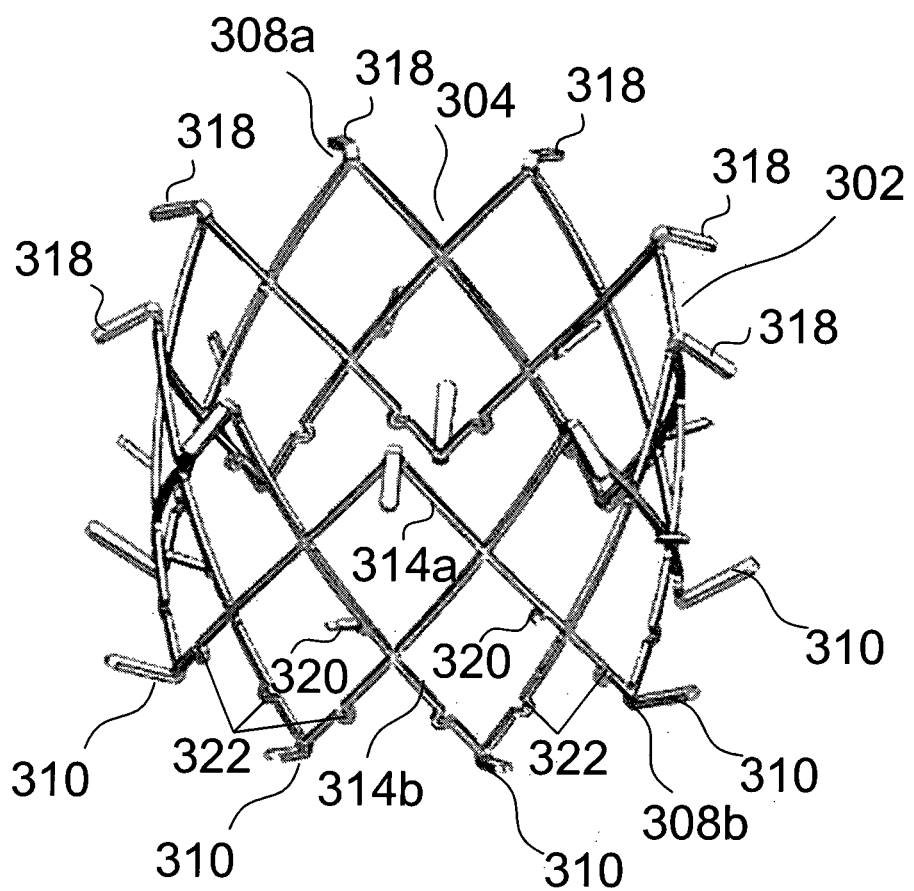
FIG. 3A shows a perspective view of a stent member according to various embodiments.
Figure 3B:
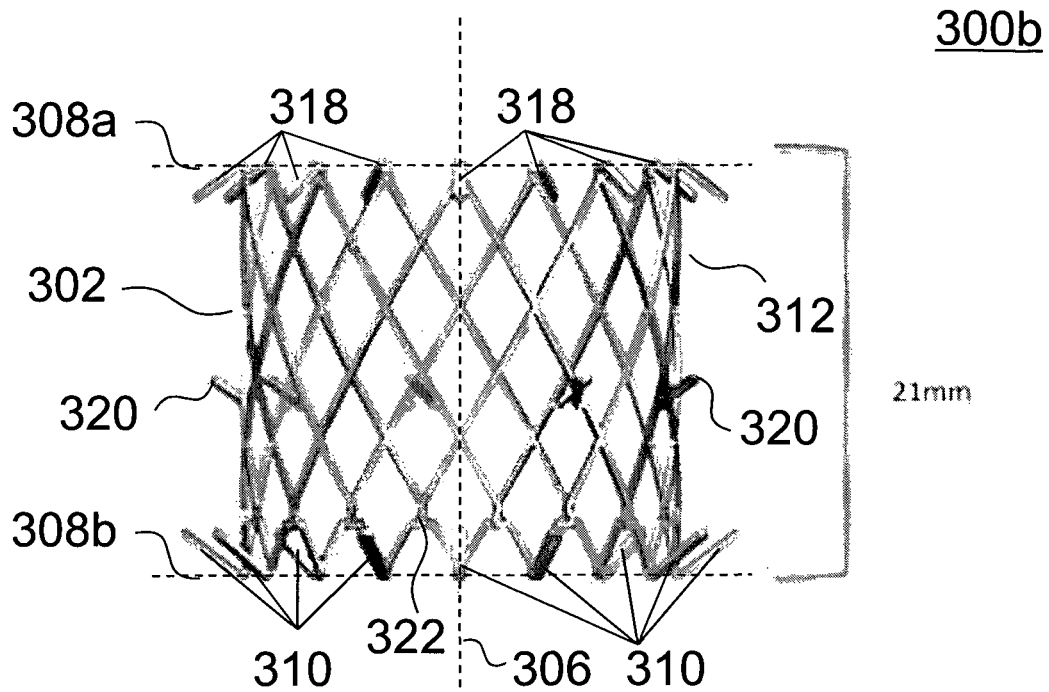
FIG. 3B shows a side view of a stent member similar to the stent member illustrated in FIG. 3A according to various embodiments.
Figure 3C:
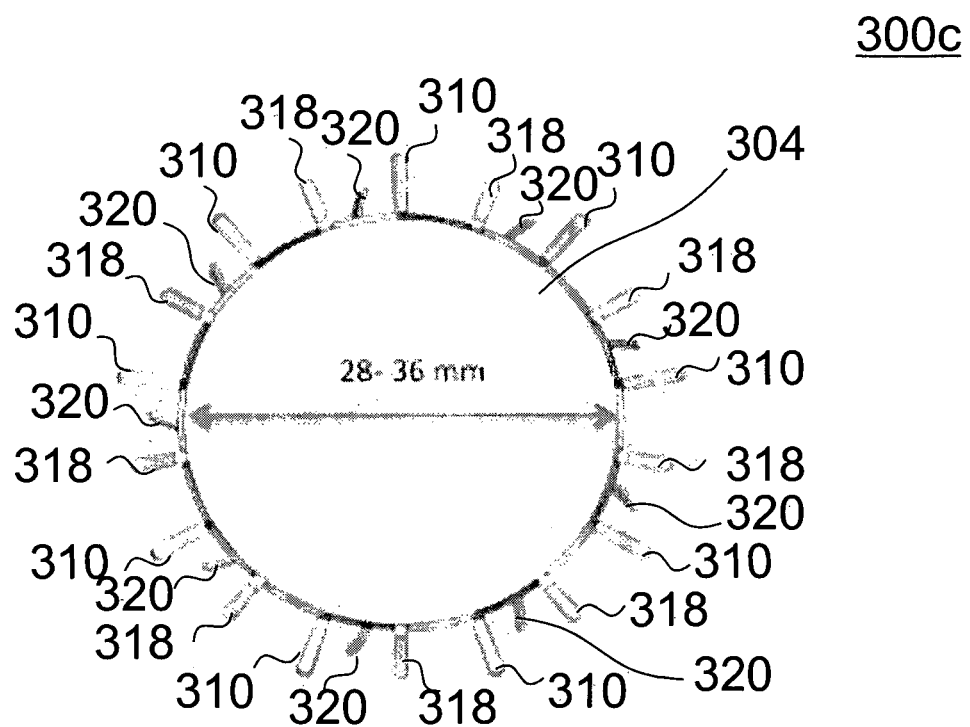
FIG. 3C shows a top view of a stent member similar to the stent member illustrated in FIG. 3A according to various embodiments.

FIG. 3A shows a perspective view 300a of a stent member according to various embodiments. FIG. 3B shows a side view 300b of a stent member similar to the stent member illustrated in FIG. 3A according to various embodiments. FIG. 3C shows a top view 300c of a stent member similar to the stent member illustrated in FIG. 3A according to various embodiments. The stent members shown in FIGS. 3A-C are in the expanded state. A stent member may include a self-expanding stent frame 302 defining in its expanded position a central annular opening 304 along a longitudinal axis 306. The annular opening may extend from a first end 308a to a second end 308b of the stent frame 302. The stent member may include a plurality of anchoring structures 310 extending radially outwards from the second end 308b of the stent frame 302. The stent member may further include a biocompatible coating 312 on the stent frame 302.

The stent frame may also include a looped arrangement 314a and a further looped arrangement 314b along the circumference of the stent frame 302 similar to the stent member shown in FIG. 2A.

The stent frame may further include additional looped arrangements. The stent frame in FIG. 3A includes two looped arrangements 314a, 314b while the stent frame in FIG. 3B includes additional looped arrangements.

A plurality of top crowns may form the first end 308a. A plurality of bottom crowns may form the second end 308b. The stent frame 302 shown in FIG. 3A may have 9 top crowns and 9 bottom crowns. A valve member may be attached or sutured on the top crowns. The valve member may additionally or alternatively be attached or sutured on the stent frame 302.

Each anchoring structure 310 may be or may include an individual strut extending or originating from or joined to each bottom crown. As seen in FIG. 3A, each anchoring structure 310 may extend or originate from the second end 308b (distal end) radially outwards and backwards in a direction towards a plane formed by the first end 308a of the stent frame 302. The anchoring structures 310 may form a conical structure. The anchoring structures 310 may be coated with a biocompatible material.

The stent member may further include a plurality of further anchoring structures 318 extending radially outwards from or joined to the first end 308a (proximal end) of the stent frame 202. Each further anchoring structure 318 may include an individual strut extending or originating radially outwards and in a direction backwards towards to a plane formed by the second end 308b of the stent member 302.

The anchoring structures 310 and/or further anchoring structures 318 may be hook-like projections. The anchoring structures 310 and/or further anchoring structures 318 may serve a dual function of anchoring the stent member to the mitral annulus and self-aligning the artificial valve during deployment.

The stent member may further include anchoring protrusions 320 extending from the stent frame 302. The protrusions 320 may extend from the struts and/or further struts making up the stent frame 302. The anchoring protrusion 320 may be hook-like protrusions that are located approximately at the mid-point of the stent struts and/or further stent struts. The anchoring protrusions 320 may serve to further secure the artificial valve onto the mitral annulus. The stent struts and/or further stent struts may also include bent portions 322. The bent portions 322 may be located on the stent struts and/or further stent struts nearer to second end 308b than the first end 308a. The bent portions 322 may also be referred to as kink-like configurations. The bent portions 322 may be configured to be substantially straight when the stent member is in the collapsed state, e.g. after device crimping. On deployment into the human or animal body (e.g. during and after expansion of the stent member), the bent portions 322 may recoil or be bent. The recoil or bending of portions 322 may facilitate enhanced engagement of the anchoring structures 310 into the mitral annulus tissues. The stent frame 302 may be coated with a biocompatible material to enhance sealing at the mitral annulus-device interface to address the issue of paravalvular leakages.

The diameter of the opening 304 may typically in the range of about 28 mm to about 36 mm, depending on the mitral annulus diameter of the patient. The stent member may have a height, measured parallel to the longitudinal axis 306, of about 21 mm. However, the dimensions indicated in FIGS. 3B and 3C are not intended to be limiting and the stent member may be of any suitable dimensions.

Figure 3D:
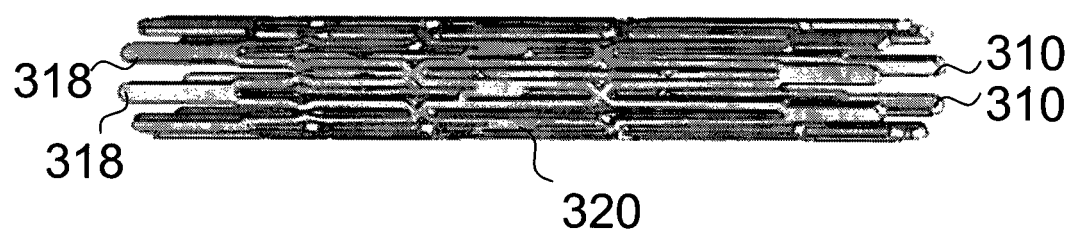
FIG. 3D shows a perspective view of a stent member similar to the stent member illustrated in FIG. 3A in a collapsed state according to various embodiments.

FIG. 3D shows a perspective view 300d of a stent member similar to the stent member illustrated in FIG. 3A in a collapsed state according to various embodiments. When the stent member is in the collapsed state, the stent struts and/or the further stent struts may be aligned parallel to the longitudinal axis 306. The diameter of the stent frame 302 when the stent member is in the collapsed state may be smaller than the diameter of the stent frame when the stent member is in the expanded state. The anchoring, structures 310 may be aligned parallel to the longitudinal axis 306 when the stent member is in the collapsed state. Further, the further anchoring structures 318 and/or the anchoring protrusions 320 may be aligned parallel to the longitudinal axis 306 when the stent member is in the collapsed state. The stent member may be configured to be deployed by a catheter in a human or animal body when the stent member is in the collapsed state.

Figure 3E:
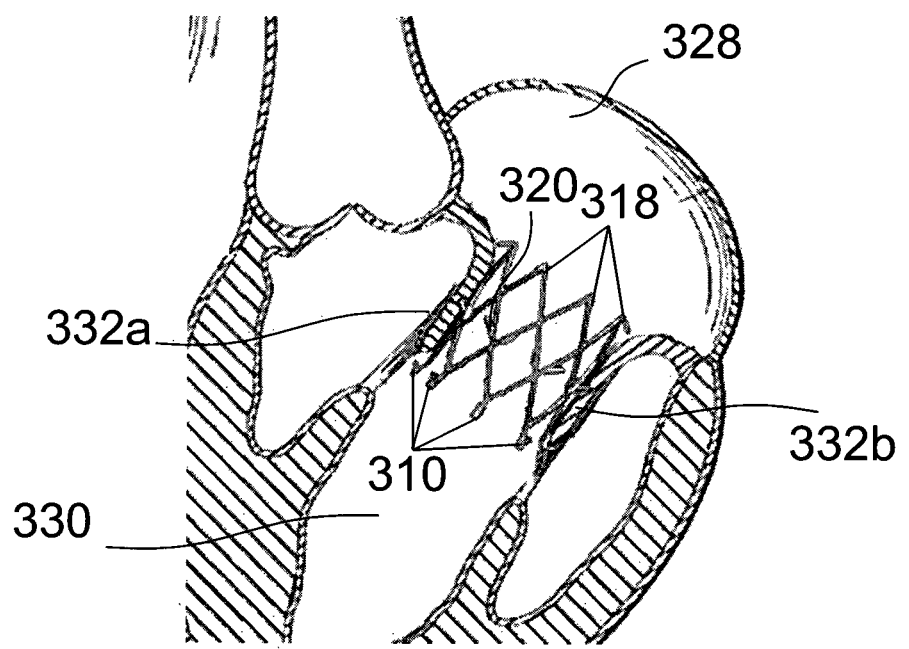
FIG. 3E shows a side view of a stent member similar to the stent member illustrated in FIG. 3A according to various embodiments being deployed as part of a percutaneous mitral valve replacement device in the heart.

FIG. 3E shows a side view 300e of a stent member similar to the stent member illustrated in FIG. 3A according to various embodiments being deployed as part of a percutaneous mitral valve replacement device in the heart. The percutaneous mitral valve replacement device may further include a valve member (not shown in FIG. 3E) attached or sutured to the stent member. As shown in FIG. 3E, the stent member may be positioned between the left atrium 328 and the left ventricle 330. The first end 308a of the stent member may be positioned within the left atrium 328 and the second end 308b of the stent member may be positioned within the left ventricle 330. The self-expanding stent frame 302 may push against the leaflets of the biological mitral valve. The anchoring structures 310 may engage the end portions of the leaflets. The anchoring protrusions 320 may be pushed by the stent frame 302 to engage the leaflets. The further anchoring structures 318 may engage portions of the left atrium 328 or the upper portions of the leaflets.

Figure 4A:
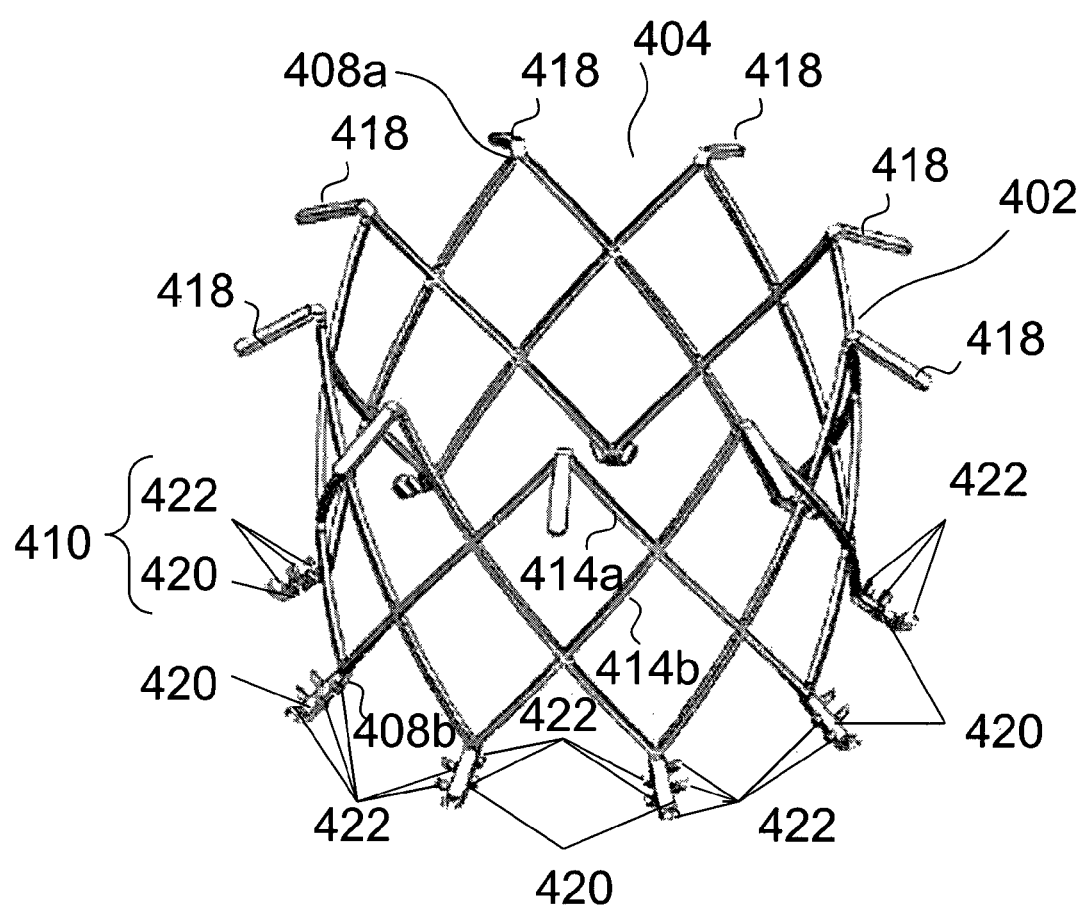
FIG. 4A shows a perspective view of a stent member according to various embodiments.
Figure 4B:
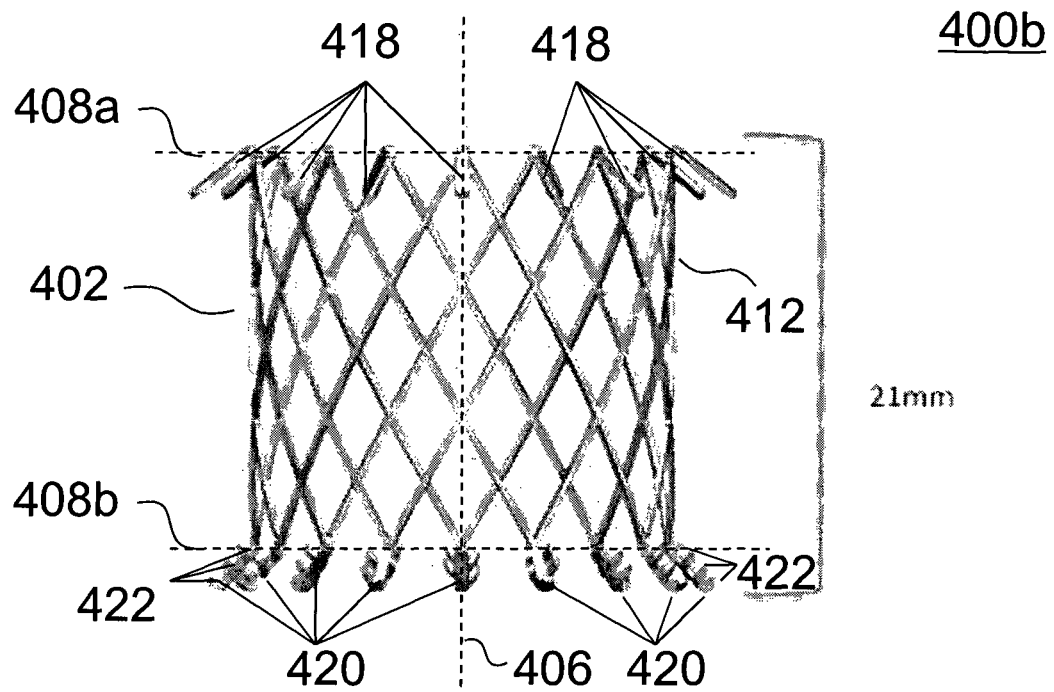
FIG. 4B shows a side view of a stent member similar to the stent member illustrated in FIG. 4A according to various embodiments.
Figure 4C:
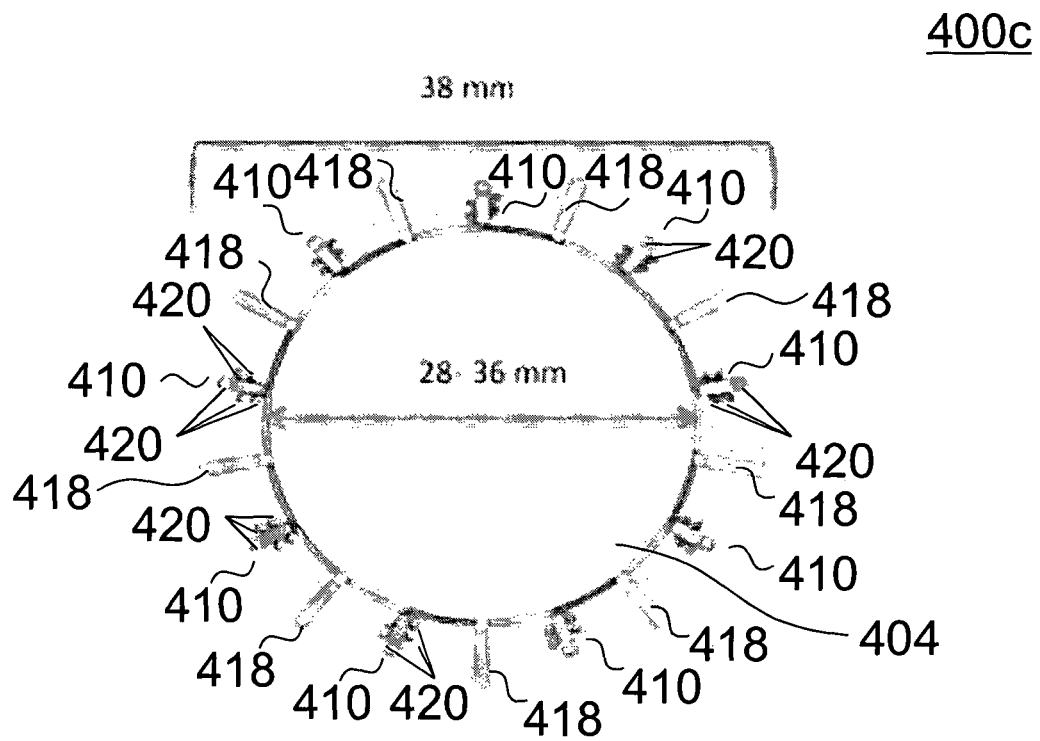
FIG. 4C shows a top view of a stent member similar to the stent member illustrated in FIG. 4A according to various embodiments.

FIG. 4A shows a perspective view 400a of a stent member according to various embodiments. FIG. 4B shows a side view 400b of a stent member similar to the stent member illustrated in FIG. 4A according to various embodiments. FIG. 4C shows a top view 400c of a stent member similar to the stent member illustrated in FIG. 4A according to various embodiments. The stent members shown in FIGS. 4A-C are in the expanded state. A stent member may include a self-expanding stent frame 402 defining in its expanded position a central annular opening 404 along a longitudinal axis 406. The annular opening may extend from a first end 408a to a second end 408b of the stent frame 402. The stent member may include a plurality of anchoring structures 410 extending radially outwards from the second end 408b of the stent frame 402. The stent member may further include a biocompatible coating 412 on the stent frame 402.

The stent frame may also include a looped arrangement 414a and a further looped arrangement 414b along the circumference of the stent frame 402 similar to the stent member shown in FIG. 2A.

The stent frame may further include additional looped arrangements. The stent frame in FIG. 4A includes two looped arrangements 414a, 414b while the stent frame in FIG. 4B includes additional looped arrangements.

A plurality of top crowns may form the first end 408a. A plurality of bottom crowns may form the second end 408b. The stent frame 402 shown in FIG. 4A may have 9 top crowns and 9 bottom crowns. A valve member may be attached or sutured on the top crowns. The valve member may additionally or alternatively be attached or sutured on the stent frame 402.

Each anchoring structure 410 may include an elongated member 420 extending or originating from or joined to each bottom crown. The elongated member 420 may extend or originate from the second end 408b (distal end) radially outwards and away from a plane formed by the first end 408a of the stent frame 402.

Each anchoring structure 410 may further include a plurality of protrusions 422 extending from the elongated member 420. The plurality of protrusions may extend towards the plane formed by the first end 408a of the stent frame 402.

In other words, each anchoring structure may include a main vertical strut structure 420 and array of hooks 422 extending from or joined to the main vertical strut.

The stent member may further include a plurality of further anchoring structures 418 extending radially outwards from or joined to the first end 408a (proximal end) of the stent frame 402. Each further anchoring structure 418 may include an individual strut extending or originating radially outwards and backwards in a direction towards to a plane formed by the second end 408b of the stent member 402.

The diameter of the opening 404 may typically in the range of about 28 mm to about 36 mm, depending on the mitral annulus diameter of the patient. The stent member may have a diameter (the distance extending between radially outermost tips of the anchoring structures or further anchoring structures) of about 38 mm. The stent member may have a height, measured parallel to the longitudinal axis 406, of about 21 mm. However, the dimensions indicated in FIGS. 4B and 4C are not intended to be limiting and the stent member may be of any suitable dimensions.

Figure 4D:
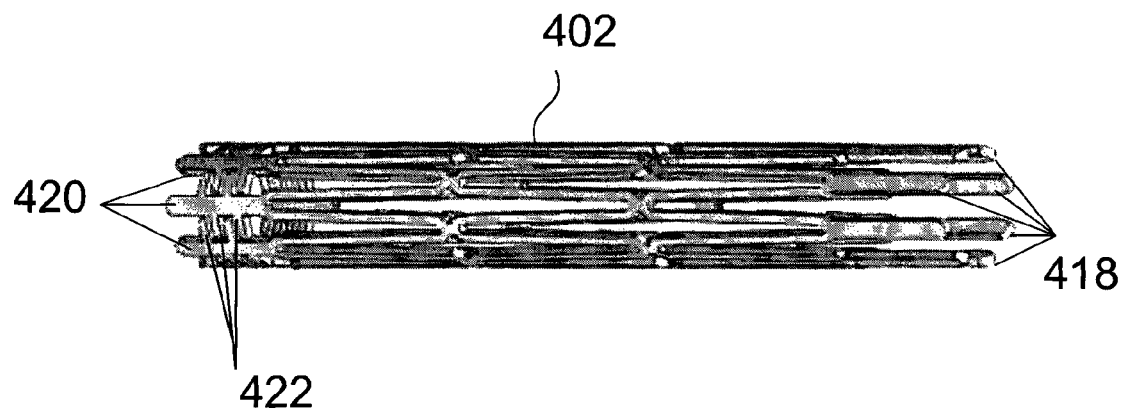
FIG. 4D shows a perspective view of a stent member similar to the stent member illustrated in FIG. 4A in a collapsed state according to various embodiments.

FIG. 4D shows a perspective view 400d of a stent member similar to the stent member illustrated in FIG. 4A in a collapsed state according to various embodiments. When the stent member is in the collapsed state, the stent struts and/or the further stent struts may be aligned substantially parallel to the longitudinal axis 406. The diameter of the stent frame 402 when the stent member is in the collapsed state may be smaller than the diameter of the stent frame when the stent member is in the expanded state. Further, the elongated members 420 of the anchoring structures 410 may be aligned parallel to the longitudinal axis 406. The protrusions or hooks 422 may interlock one another as shown in FIG. 4D. The protrusions or hooks 422 may face inwards (towards longitudinal axis 406) so that the anchoring structures 410 is substantially flush with the stent frame 402. Also, the further anchoring structures 418 may also be aligned substantially parallel to the longitudinal axis 406.

Figure 4E:
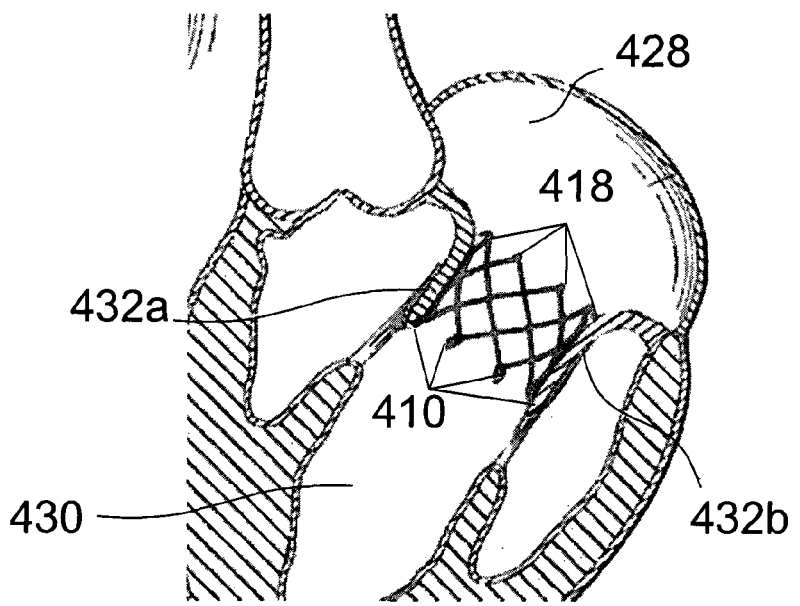
FIG. 4E shows a side view of a stent member similar to the stent member illustrated in FIG. 4A according to various embodiments being deployed as part of a percutaneous mitral valve replacement device in the heart.

FIG. 4E shows a side view 400e of a stent member similar to the stent member illustrated in FIG. 4A according to various embodiments being deployed as part of a percutaneous mitral valve replacement device in the heart. The percutaneous mitral valve replacement device may further include a valve member (not shown in FIG. 4E) attached or sutured to the stent member. As shown in FIG. 4E, the stent member may be positioned between the left atrium 428 and the left ventricle 430. The first end 408a of the stent member may be positioned within the left atrium 428 and the second end 408b of the stent member may be positioned within the left ventricle 430. The self-expanding stent frame 402 may push against the leaflets of the biological mitral valve. The protrusions 422 of anchoring structures 410 may anchor the device onto surrounding mitral annulus tissues as well as to prevent device migration in the distal direction during ventricle systole.

The further anchoring structures 418 may engage portions of the left atrium 228. The further anchoring structures may self-align the device onto the mitral annulus as well as to prevent the distal migration of the device into the ventricle.

The biocompatible coating 412 may form a tight seal at the interface between the mitral annulus and the device to help address the issue of paravalvular leakages.

Figure 5A:
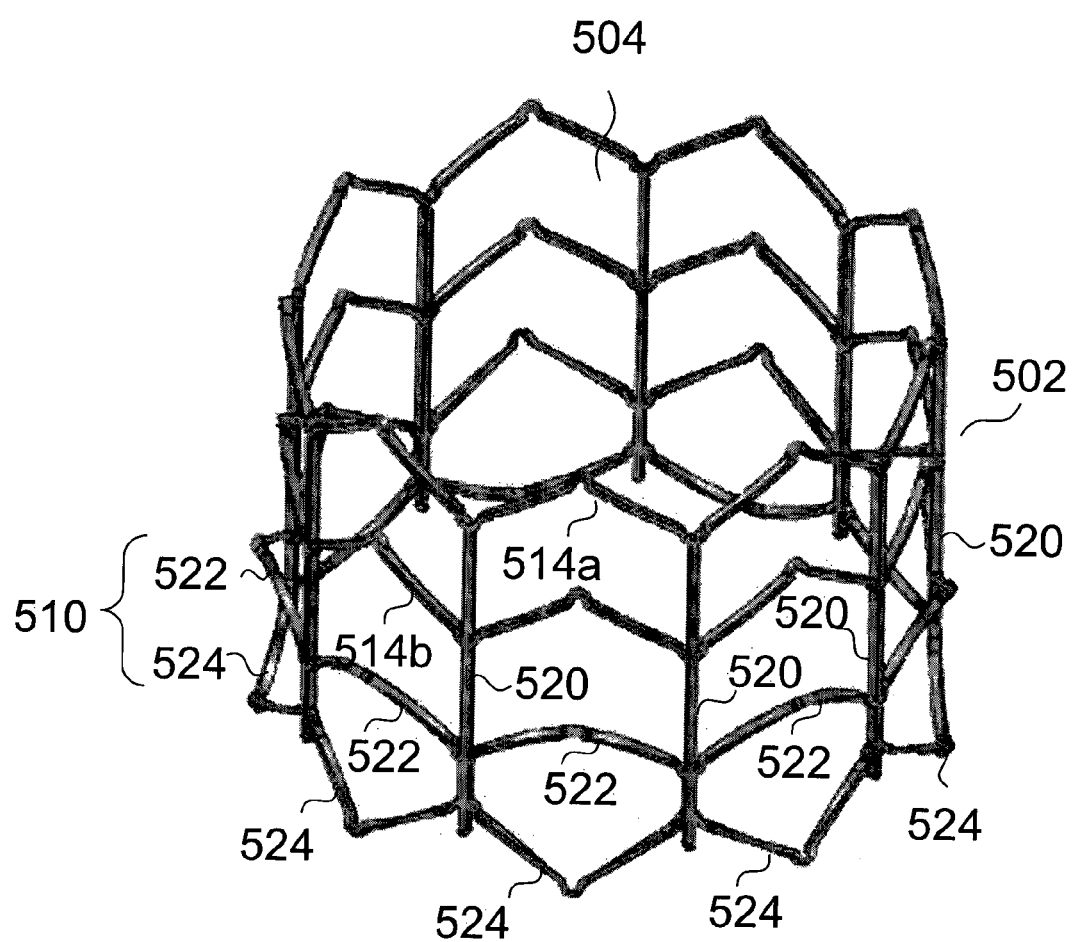
FIG. 5A shows a perspective view of a stent member according to various embodiments.
Figure 5B:
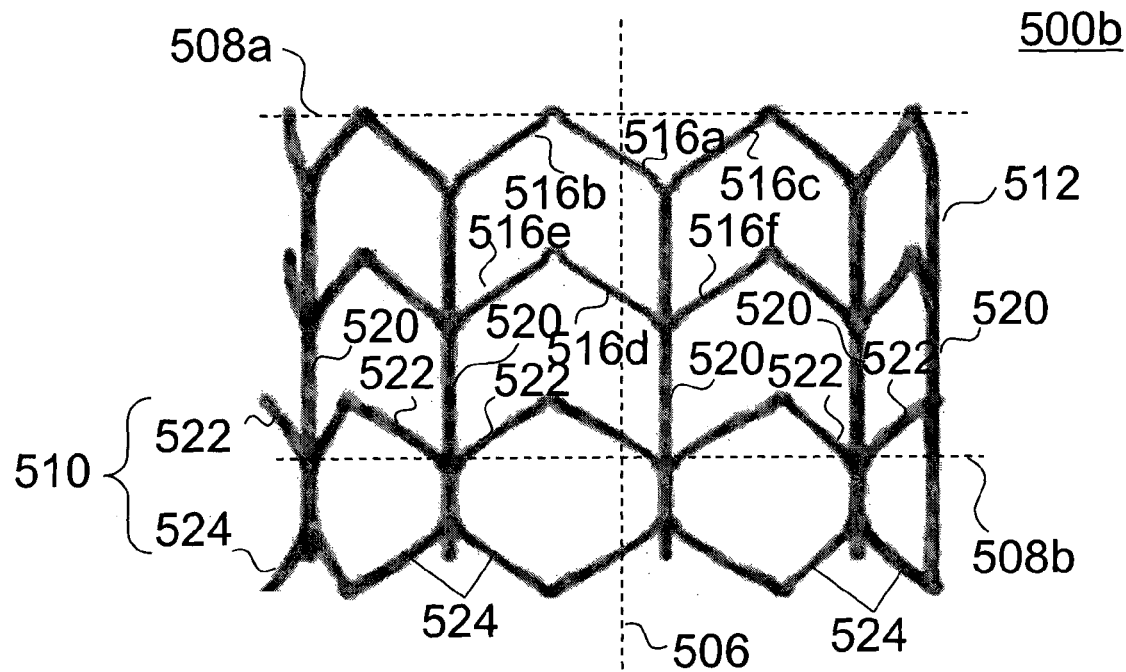
FIG. 5B shows a side view of a stent member similar to the stent member illustrated in FIG. 5A according to various embodiments.
Figure 5C:
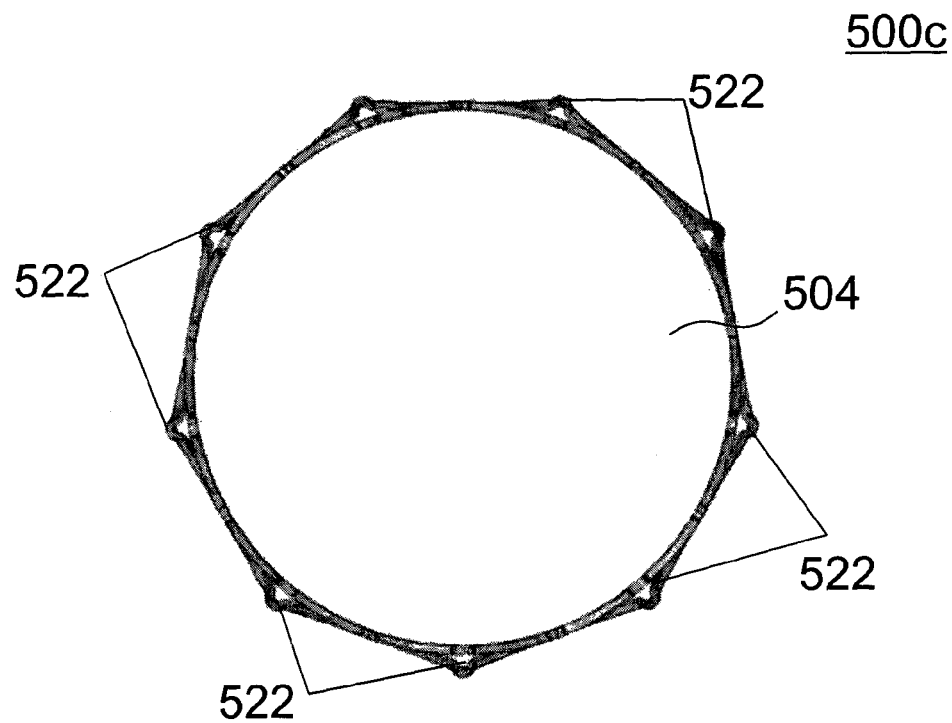
FIG. 5C shows a top view of a stent member similar to the stent member illustrated in FIG. 5A according to various embodiments.

FIG. 5A shows a perspective view 500a of a stent member according to various embodiments. FIG. 5B shows a side view 500b of a stent member similar to the stent member illustrated in FIG. 5A according to various embodiments. FIG. 5C shows a top view 500c of a stent member similar to the stent member illustrated in FIG. 5A according to various embodiments. The stent members shown in FIGS. 5A-C are in the expanded state. A stent member may include a self-expanding stent frame 502 defining in its expanded position a central annular opening 504 along a longitudinal axis 506. The annular opening may extend from a first end 508a to a second end 508b of the stent frame 502. The stent member may include a plurality of anchoring structures 510 extending radially outwards from the second end 508b of the stent frame 502. The stent member may further include a biocompatible coating 512 on the stent frame 502. In other words, the stent frame 502 may be reinforced or insulated with the biocompatible coating 512.

The stent frame 502 may include a looped arrangement 514a along a circumference of the stent frame 502, the looped arrangement 514a including a plurality of stent struts, e.g. 516a, 516b, 516c, each stent strut having a first end joined to a first neighbouring stent strut and a second end joined to a second neighbouring stent strut. For instance, stent strut 516a may have a first end joined to a first neighbouring stent strut 516b and a second end joined to a second neighbouring stent strut 516c. Each stent strut may be joined to the first neighbouring stent strut at a first obtuse angle, and each stent strut may be joined to the second neighbouring stent strut at a second obtuse angle. For instance, stent strut 516a may be joined to the first neighbouring stent strut 516b at a first obtuse angle to form a top crown. The first obtuse angle may be the same as the second obtuse angle. In other words, the loop arrangement 514a may include a plurality of stent struts joined to one another to define a circumference of the stent frame 502. As shown in FIGS. 5A and 5B, the loop arrangement 514a may form a closed zig-zag pattern along the circumference.

The stent frame may also include a further looped arrangement 514b along the circumference of the stent frame 502. The further looped arrangement 514b may include a plurality of further stent struts, e.g. 516d, 516e, 516f. Each further stent strut having a first end joined to a further first neighbouring stent strut and a second end joined to a further second neighbouring stent strut. For instance, stent strut 516d may have a first end joined to a first neighbouring stent strut 516e and a second end joined to a second neighbouring stent strut 516f. Each further stent strut may be joined to the further first neighbouring stent strut at a first obtuse angle, and each further stent strut may be joined to the further second neighbouring stent strut at a second obtuse angle. The further stent strut 516d may be joined to the further second neighbouring stent strut 516f to form a bottom crown. In other words, the further loop arrangement 514b may include a plurality of further stent struts joined to one another to define a circumference of the stent frame 502. As shown in FIGS. 5A and 5B, the further loop arrangement 514b may form a closed zig-zag pattern along the circumference similar to that for the looped arrangement 514a.

The stent frame 502 may further include a plurality of axial struts 520 aligned substantially parallel to the longitudinal axis 506 of the stent member 502. The axial struts 520 may be aligned to the longitudinal axis 506 when the stent member is both in the expanded state and the collapsed state. The stent struts of the looped arrangement 514a may be joined to the further stent struts of the further looped arrangement 514b via the axial struts 520 to form the plurality of cells. In other words, the stent struts of the looped arrangement may be joined indirectly to the further stent struts of the further looped arrangement via the axial struts 520. For instance, stent struts 514a, 514c of looped arrangement 514a may be joined to further stent struts 514d, 514f of further looped arrangement 514b via an axial stent strut 520.

The stent frame 502 may further include additional looped arrangements. Each looped arrangement may be joined to neighbouring looped arrangement via the axial stent struts 520.

A plurality of top crowns may form the first end 508a. A plurality of bottom crowns may form the second end 508b. A valve member may be attached or sutured on the top crowns and/or on the stent frame 502.

Each anchoring structure 510 may be or may include an anchorage mechanism include upper radial projections 522 and lower radial projections 524. The upper radial projections 522 and lower radial projections 524 may be wing-like radial projections. The anchoring structures 510 may help to secure the device onto the mitral annulus.

Each upper radial projection 522 and/or each lower radial projection 524 may extend or originate from the second end 508b (distal end) radially outwards. Each lower radial projection 524 may extend away from a plane formed by the first end 508a of the stent frame 502. Each upper radial projection 522 may extend towards the plane formed by the first end 508a of the stent frame 502. Axial struts 520 may join upper radial projections 522 with lower radial projections 524 and the main stent frame 520. Each radial projection 522, 524 may include a single length of stent material joined to neighbouring axial struts 520 or may include two connected struts joined to or extending from neighbouring axial struts 520. Each lower radial projection 524 may have a length substantially equal to a length of each upper radial projection 522.

The device may be coated with the biocompatible material 512 to enhance sealing at the device-mitral interface to minimize paravalvular leakages.

Figure 5D:
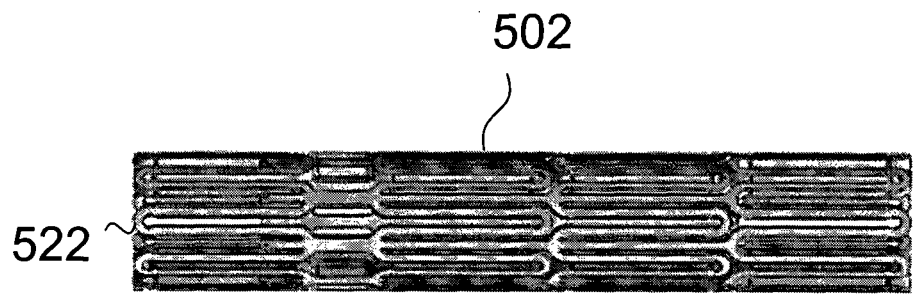
FIG. 5D shows a perspective view of a stent member similar to the stent member illustrated in FIG. 5A in a collapsed state according to various embodiments.

FIG. 5D shows a perspective view 500d of a stent member similar to the stent member illustrated in FIG. 5A in a collapsed state according to various embodiments. As seen from FIG. 5D, the stent struts and/or the further stent struts may be aligned parallel to the longitudinal axis 506 when the stent member is in a collapsed state. The diameter of the stent frame 502 when the stent member is in the collapsed state may be smaller than the diameter of the stent frame when the stent member is in the expanded state. The anchoring structure 510 including upper radial projections 522 and lower radial projections 524 may also be aligned to the longitudinal axis 506. In other words, the struts forming the upper radial projections 522 and lower radial projections 524 may be aligned parallel to the longitudinal axis 506. The upper radial projections 522 and lower radial projections 524 may be substantially flush with the outer circumference of the stent frame when the stent member is in the collapsed state. In other words, the upper radial projections 522 and lower radial projections 524 may not protrude radially outwards when the stent member is in a collapsed state, which may facilitate deployment of the stent member in a human or animal body. The stent member may be configured to be deployed by a catheter in the human or animal body when the stent member is in the collapsed state.

Figure 5E:
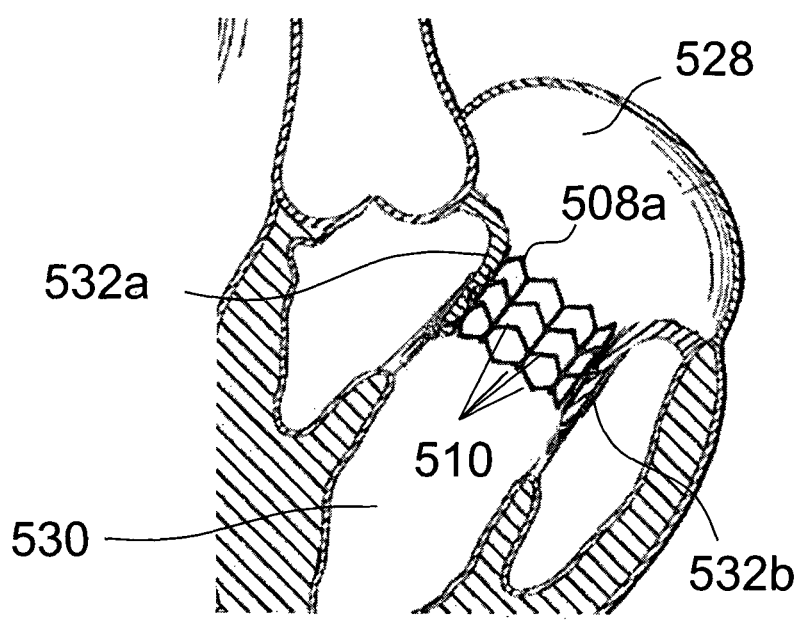
FIG. 5E shows a side view of a stent member similar to the stent member illustrated in FIG. 5A according to various embodiments being deployed as part of a percutaneous mitral valve replacement device in the heart.

FIG. 5E shows a side view 500e of a stent member similar to the stent member illustrated in FIG. 5A according to various embodiments being deployed as part of a percutaneous mitral valve replacement device in the heart. The percutaneous mitral valve replacement device may further include a valve member (not shown in FIG. 5E) attached or sutured to the stent member. The stent member may be positioned between the left atrium 528 and the left ventricle 530. The self-expanding stent frame 502 may push against the leaflets of the biological mitral valve. The anchoring structures 510 may anchor to the leaflets of the mitral valve.

Figure 6:
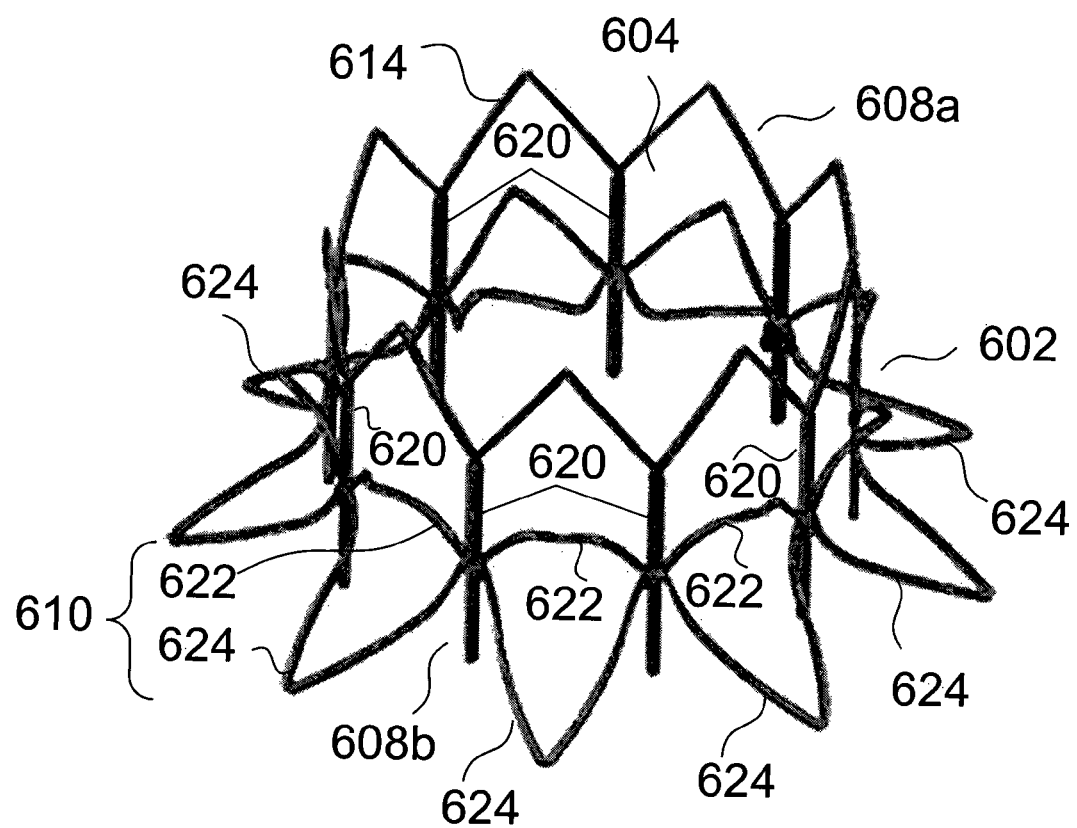
FIG. 6 shows a perspective view of a stent member according to various embodiments.

FIG. 6 shows a perspective view 600 of a stent member according to various embodiments. The stent member shown in FIG. 6 is in the expanded state. A stent member may include a self-expanding stent frame 602 defining in its expanded position a central annular opening 604 along a longitudinal axis. The annular opening may extend from a first end 608a to a second end 608b of the stent frame 602. The stent member may include a plurality of anchoring structures 610 extending radially outwards from the second end 608b of the stent frame 602. The stent member may further include a biocompatible coating on the stent frame 602.

The stent frame 602 may include a looped arrangement 614 along a circumference of the stent frame 602, the looped arrangement 614 including a plurality of stent struts (similar to the looped arrangement 514 shown in FIGS. 5A-B). The stent frame 602 may further include a plurality of axial struts 620 aligned substantially parallel to the longitudinal axis of the stent member 602. The axial stent struts 620 may join the looped arrangement 614 to the anchoring structures 610.

Each anchoring structure 610 may be or may include an anchorage mechanism include upper radial projections 622 and lower radial projections 624. The upper radial projections 622 and lower radial projections 624 may be wing-like radial projections. The anchoring structures 610 may help to secure the device onto the mitral annulus.

Each lower radial projection 624 may extend away from a plane formed by the first end 608a of the stent frame 602. Each upper radial projection 622 may extend towards the plane formed by the first end 608a of the stent frame 602. Axial struts 620 may join upper radial projections 622 with lower radial projections 624 and the main stent frame 620. Each radial projection 622, 624 may include a single length of stent material joined to neighbouring axial struts 620 or may include two connected struts joined to neighbouring axial struts 620. Each lower radial projection 624 may have a greater length compared to each upper radial projection 622. The difference in lengths between lower radial projections 624 and upper radial projections 622 may exceed a predefined value. The longer lower radial projections 624 may provide better anchoring of the device and may prevent the device from being dislodged, for instance into the right atrium.

Figure 7:
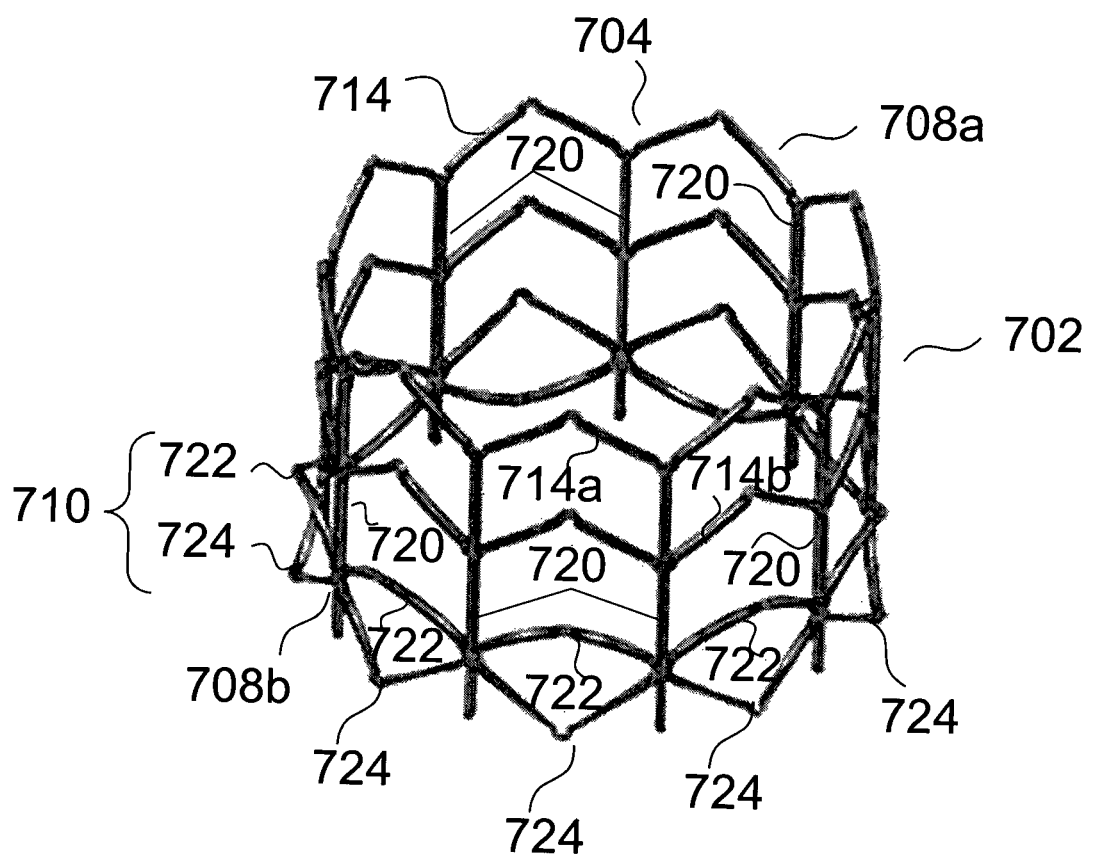
FIG. 7 shows a perspective view of a stent member according to various embodiments.

FIG. 7 shows a perspective view 700 of a stent member according to various embodiments. The stent member shown in FIG. 7 is in the expanded state. A stent member may include a self-expanding stent frame 702 defining in its expanded position a central annular opening 704 along a longitudinal axis. The annular opening may extend from a first end 708a to a second end 708b of the stent frame 702. The stent member may include a plurality of anchoring structures 710 extending radially outwards from the second end 708b of the stent frame 702. The stent member may further include a biocompatible coating on the stent frame 702.

The stent frame 702 may include a looped arrangement 714a along a circumference of the stent frame 702, the looped arrangement 714a including a plurality of stent struts. The stent frame 702 may also include a further looped arrangement 714b along the circumference of the stent frame, the further looped arrangement 714b including a plurality of further stent struts. The stent frame 702 may further include a plurality of axial struts 720 aligned substantially parallel to the longitudinal axis of the stent member 702.

The axial stent struts 720 may join the looped arrangement 714*a* to the looped arrangement 714*b*. The axial stent struts 720 may also join the anchoring structures 710. The axial stent struts 720 may be longer than the axial stent struts 520 shown in FIG. 5A and may extend beyond a predefined distance from second end 708*b*. The axial stent struts 720 may be greater than 21 mm, e.g. greater than 23 mm. The longer axial stent struts 720 may advantageously provide greater tolerance for movement of the stent member within annulus of the biological valve before being dislodged.

The anchoring structures 710 are similar to the anchoring structures 510 shown in FIG. 5A. Each anchoring structure 710 may be or may include an anchorage mechanism include upper radial projections 722 and lower radial projections 724. The upper radial projections 722 and lower radial projections 724 may be wing-like radial projections. The anchoring structures 710 may help to secure the device onto the mitral annulus.

Each lower radial projection 724 may extend away from a plane formed by the first end 708*a* of the stent frame 702. Each upper radial projection 722 may extend towards the plane formed by the first end 708*a* of the stent frame 702. Axial struts 720 may join upper radial projections 722 with lower radial projections 724 and the main stent frame 720. Each radial projection 722, 724 may include a single length of stent material joined to neighbouring axial struts 720 or may include two connected struts joined to neighbouring axial struts 720.

Figure 8A:
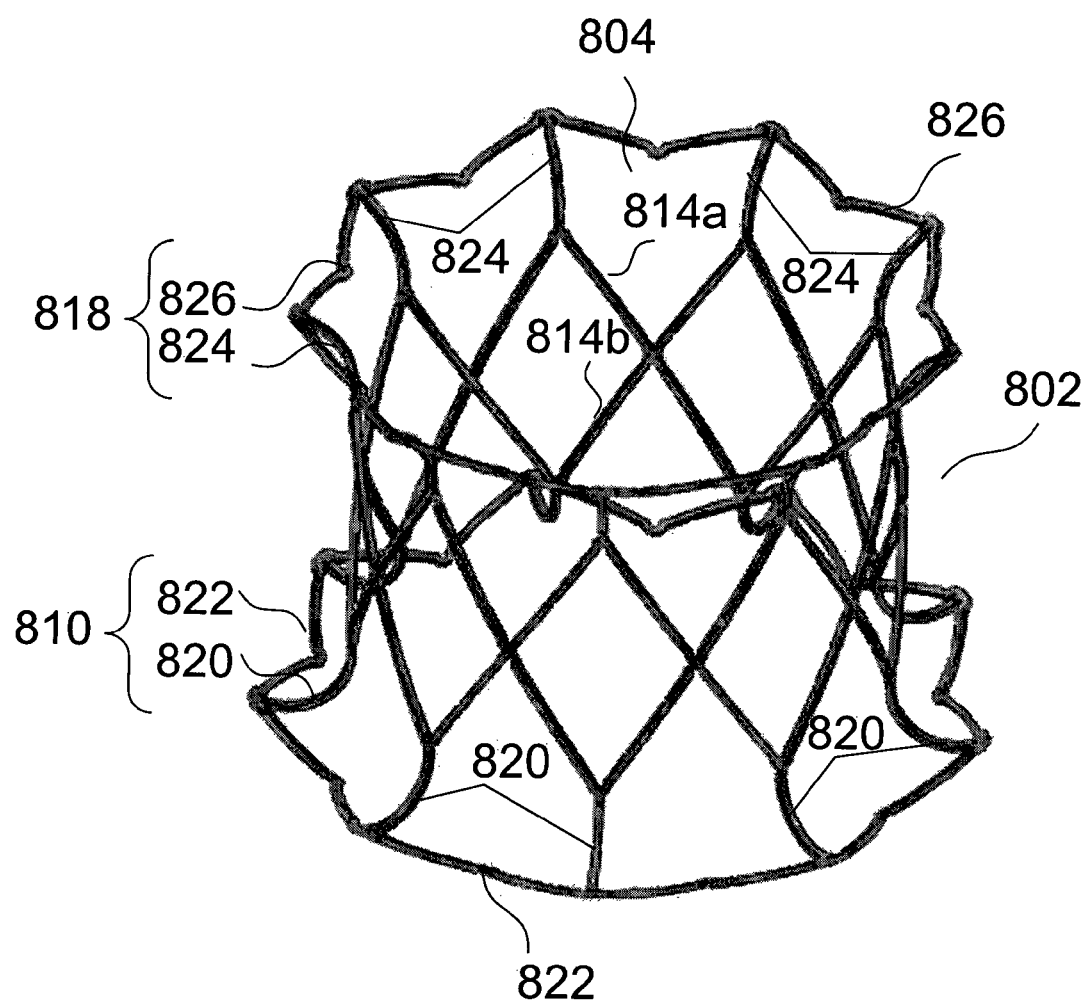
FIG. 8A shows a perspective view of a stent member according to various embodiments.
Figure 8B:
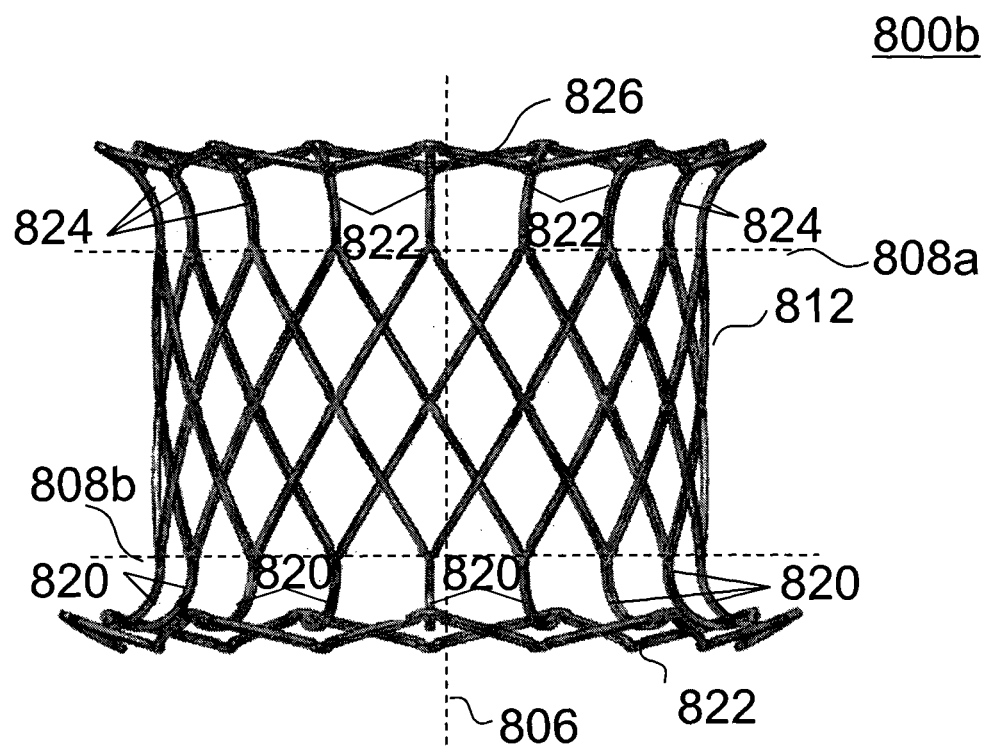
FIG. 8B shows a side view of a stent member similar to the stent member illustrated in FIG. 8A according to various embodiments.
Figure 8C:
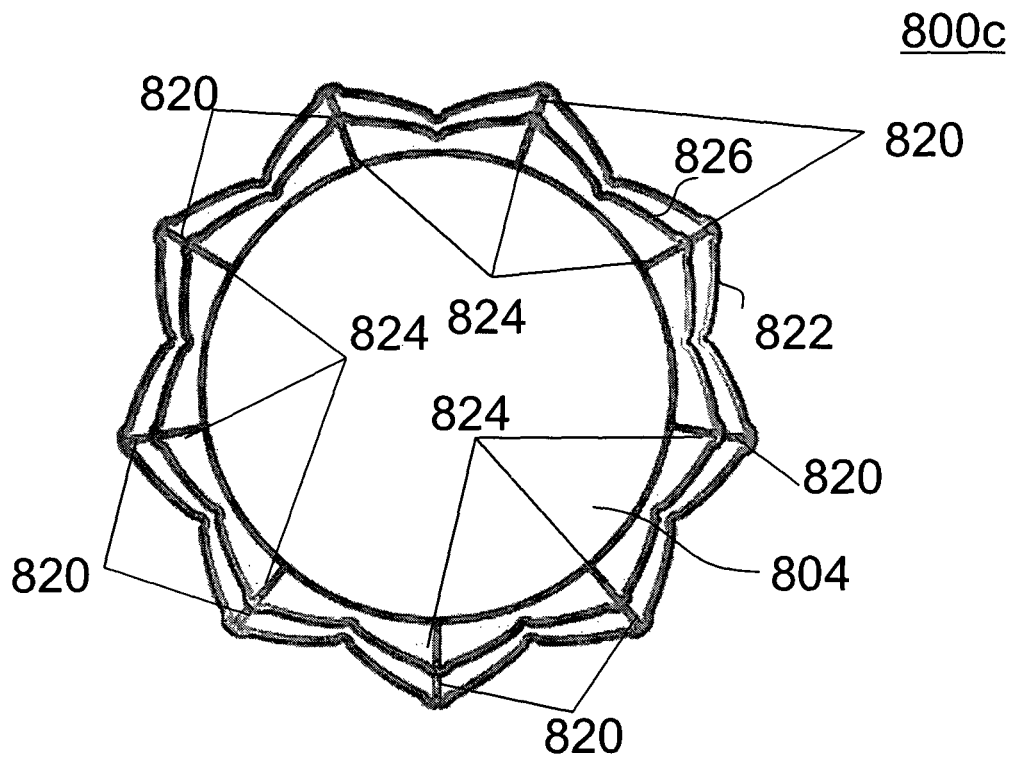
FIG. 8C shows a top view of a stent member similar to the stent member illustrated in FIG. 8A according to various embodiments.

FIG. 8A shows a perspective view 800*a* of a stent member according to various embodiments. FIG. 8B shows a side view 800*b* of a stent member similar to the stent member illustrated in FIG. 8A according to various embodiments. FIG. 8C shows a top view 800*c* of a stent member similar to the stent member illustrated in FIG. 8A according to various embodiments. The stent members shown in FIGS. 8A-C are in the expanded state. A stent member may include a self-expanding stent frame 802 defining in its expanded position a central annular opening 804 along a longitudinal axis 806. The annular opening may extend from a first end 808*a* to a second end 808*b* of the stent frame 802. The stent member may include an anchoring structure 810 extending radially outwards from the second end 808*b* of the stent frame 802. The stent member may further include a biocompatible coating 812 on the stent frame 802.

The stent frame may also include a looped arrangement 814*a* and a further looped arrangement 814*b* along the circumference of the stent frame 802.

The stent frame may further include additional looped arrangements. The stent frame in FIG. 8A includes two looped arrangements 814*a*, 814*b* while the stent frame in FIG. 8B includes additional looped arrangements. The looped arrangement 814*a* may be joined directly to the further looped arrangement 814*b*.

A plurality of top crowns may form the first end 808*a*. A plurality of bottom crowns may form the second end 808*b*.

The anchoring structure 810 may include a plurality of support members 820 joining or extending from the second end 808*b* of the stent frame 802, e.g. from the bottom crowns for the stent frame 802. The anchoring structure 810 may further include a skirt member 822 joined to the plurality of support members 820. The plurality of support members 820 may curve radially outwards from the stent frame 802. In addition, the plurality of support members 820 may curve away from a plane formed by the first end 808*a* of the stent frame 802. In various embodiments, the plurality of support members 820 may first curve away from a plane formed by the first end 808*a* and then curve towards the plane formed by the first end 808*a* to form J-shaped hook structures. The skirt member 822 may include a plurality of struts joined to one another. A pair of struts may joined together to form a portion of skirt member 822 between two neighbouring support members 820. The pair of struts may extend inwards from the two neighbouring support members 820 and may be joined at a point within the circumference formed by the outwards tips of the plurality of support members 820.

The stent member may further include a further anchoring structure 818 extending radially outwards from the first end 808*a* (proximal end) of the stent frame 802. Each further anchoring structure 818 may include a plurality of further support members 824 joining or extending from the first end 808*a* of the stent frame 802, e.g. from the top crowns for the stent frame 802. The further anchoring structure 818 may further include a further skirt member 826 joined to the plurality of further support members 824. The plurality of further support members 824 may curve radially outwards from the stent frame 802. In addition, the plurality of further support members 824 may curve away from a plane formed by the second end 808*b* of the stent frame 802. In various embodiments, the plurality of support members further 824 may first curve away from a plane formed by the second end 808*b* and then curve towards the plane formed by the second end 808*b* to form J-shaped hook structures. The further skirt member 826 may include a plurality of struts joined to one another. A pair of struts may joined together to form a portion of further skirt member 826 between two neighbouring further support members 824. The pair of struts may extend inwards from the two neighbouring further support members 824 and may be joined at a point within the circumference formed by the outwards tips of the plurality of further support members 824.

The anchoring structure 810 may also be referred to as a flare-type ventricular anchor. The further anchoring structure 818 may also be referred to as a flare-type atrial anchor. The anchoring structure 810 and further anchoring structure 818 may provide self-alignment of the device onto the mitral annulus during deployment, and help reduce or prevent axial migration of the device post deployment. The anchoring structure 810 and further anchoring structure 818 may also be coated with a biocompatible material to create a skirt for reducing minimizing paravalvular leakages.

The diameter of the skirt member 822 may be greater than the diameter of the further skirt member 826.

Figure 8D:
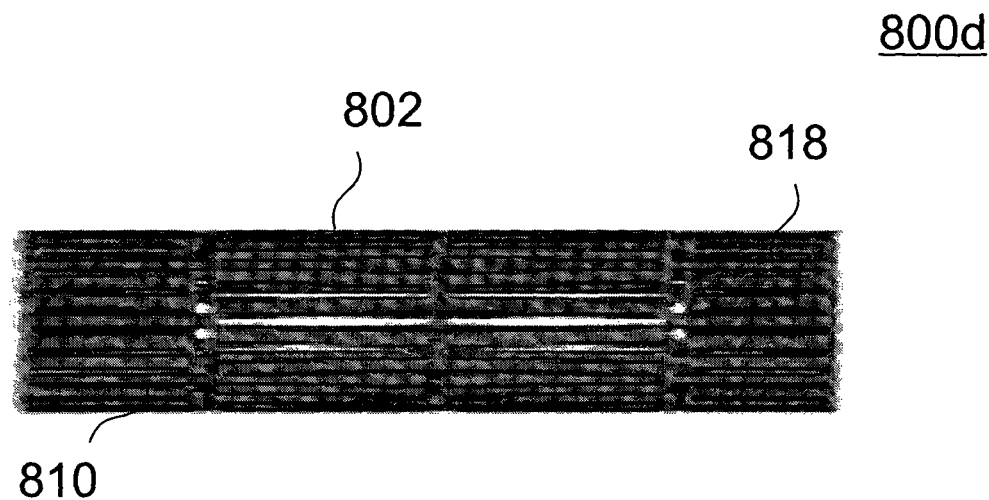
FIG. 8D shows a perspective view of a stent member similar to the stent member illustrated in FIG. 8A in a collapsed state according to various embodiments.

FIG. 8D shows a perspective view 800*d* of a stent member similar to the stent member illustrated in FIG. 8A in a collapsed state according to various embodiments. When the stent member is in the collapsed state, the stent struts and/or the further stent struts may be aligned substantially parallel to the longitudinal axis 806. The diameter of the stent frame 802 when the stent member is in the collapsed state may be smaller than the diameter of the stent frame when the stent member is in the expanded state. The anchoring structure 810 and further anchoring structure 818 may be bent or folded so that the anchoring structure 810 and further anchoring structure 818 are substantially flush with the circumference of the stent frame 802.

Figure 8E:
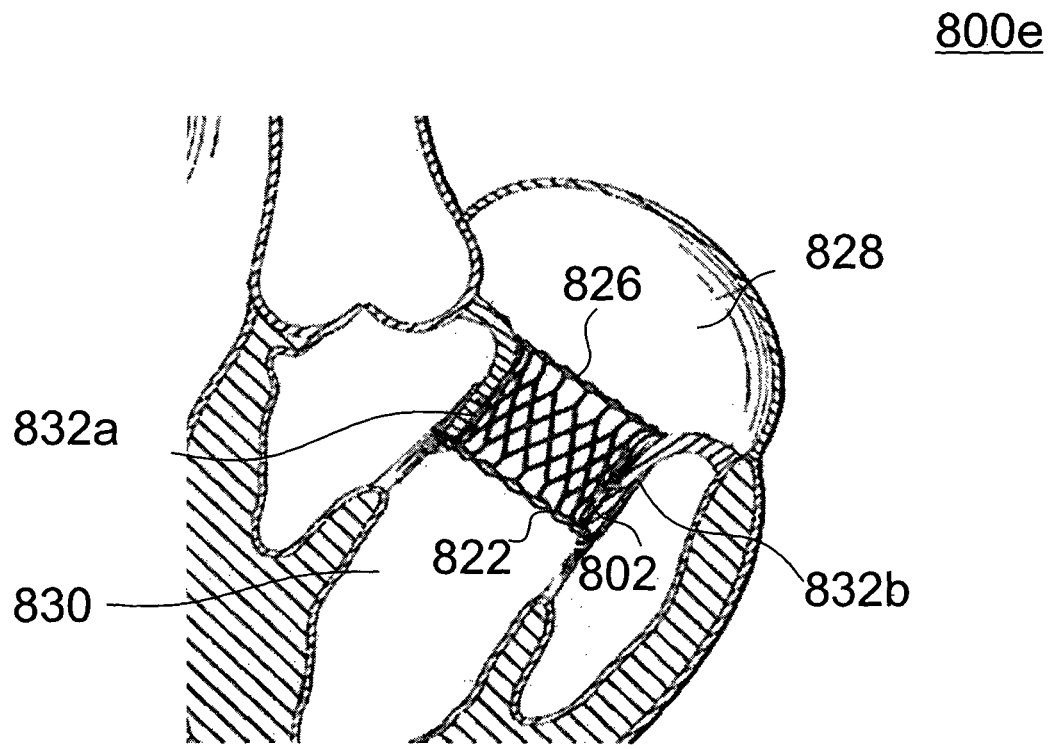
FIG. 8E shows a side view of a stent member similar to the stent member illustrated in FIG. 8A according to various embodiments being deployed as part of a percutaneous mitral valve replacement device in the heart.

FIG. 8E shows a side view 800*e* of a stent member similar to the stent member illustrated in FIG. 8A according to various embodiments being deployed as part of a percutaneous mitral valve replacement device in the heart. The percutaneous mitral valve replacement device may further include a valve member (not shown in FIG. 8E) attached or sutured to the stent member. As shown in FIG. 8E, the stent member may be positioned between the left atrium 828 and the left ventricle 830. The self-expanding stent frame 802 may push against the leaflets of the biological mitral valve. The anchoring structure 810 and further anchoring structure 818 each have a diameter greater than the diameter of the stent frame. As such, movement of the stent member towards the right atrium or right ventricle may be reduced or prevented.

Figure 9:
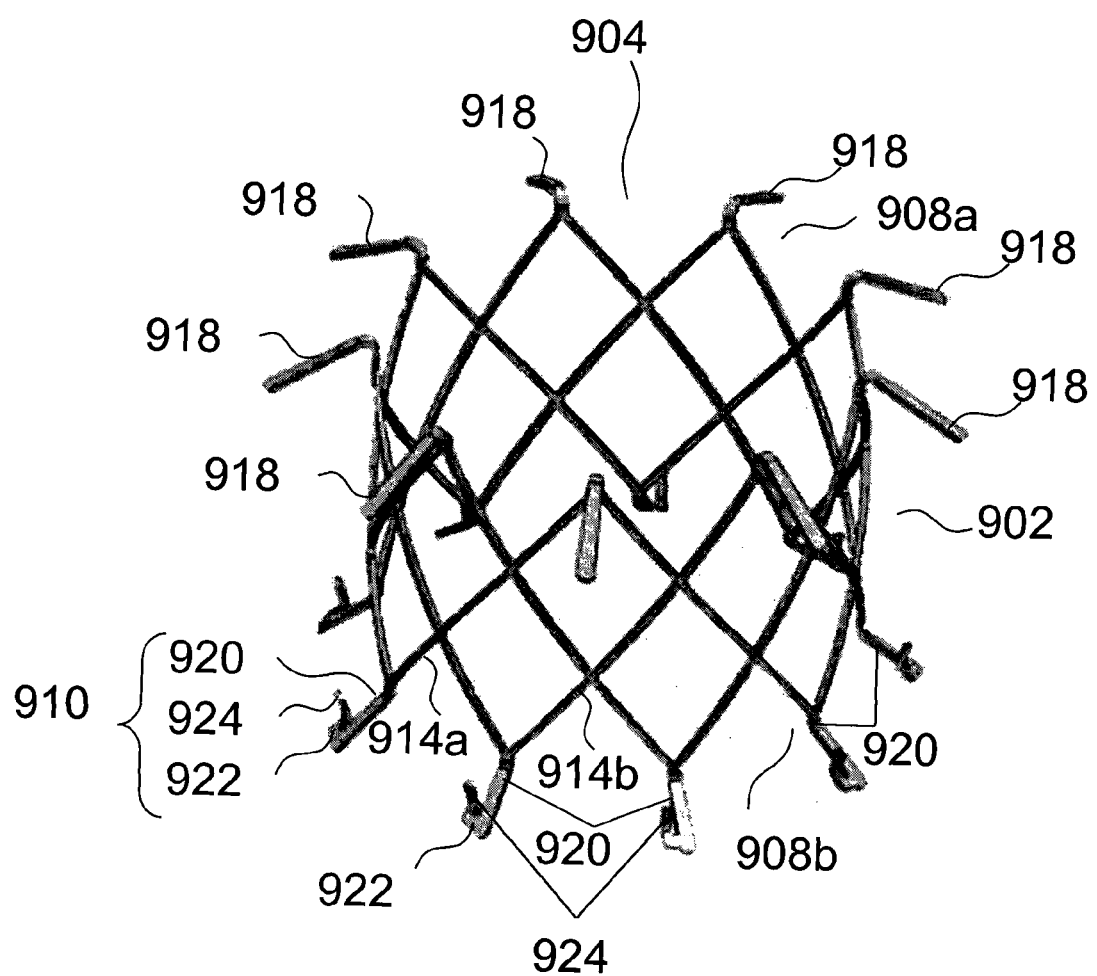
FIG. 9 shows a perspective view of a stent member according to various embodiments.

FIG. 9 shows a perspective view 900 of a stent member according to various embodiments. The stent member shown in FIG. 9 is in the expanded state. A stent member may include a self-expanding stent frame 902 defining in its expanded position a central annular opening 904 along a longitudinal axis. The annular opening may extend from a first end 908*a* to a second end 908*b* of the stent frame 902. The stent member may include a plurality of anchoring structures 910 extending radially outwards from the second end 908*b* of the stent frame 902. The stent member may further include a biocompatible coating on the stent frame 902.

The stent frame 902 may include a looped arrangement 914*a* along a circumference of the stent frame 902, the looped arrangement 914*a* including a plurality of stent struts. The stent frame 902 may also include a further looped arrangement 914*b* along the circumference of the stent frame 902, the further looped arrangement 914*b* including a plurality of further stent struts. The stent struts and plurality of stent struts may form a plurality of top crowns at the first end 908*a* and a plurality of bottom crowns at the second end 1008*b*.

Each anchoring structure 910 may include a first portion extending radially outwards and away from a plane formed by the first end 908*a*. The first portion 920 may extend from or may be joined to the stent frame 902, e.g. from the bottom crowns of the stent frame 902. Each anchoring structure 910 may include a second portion 922 extending or joining the first portion 920. The second portion 922 may extend back towards the stent frame 902. The second portion 922 may extend in parallel to the first portion 920. Each anchoring structure 910 may also include a third portion 924 extending or joining the second portion 922. The third portion 924 may extend perpendicularly to the second portion 922. The third portion 924 may extend radially outwards away from the stent frame 902 and towards the plane formed by the first end 908*a*. The first portion 920, the second portion 922, and the third portion 924 may form a twisted anchoring structure 910, which may help the device to anchor to biological tissues, such as the leaflets of the mitral valve better.

The stent member may further include a plurality of further anchoring structures 918 extending radially outwards from the first end 908*a* of the stent frame 902. Each further anchoring structure 918 may include an individual strut or curved hooked structure extending or originating radially outwards and backwards in a direction towards to a plane formed by the second end 908*b* of the stent member 902. Each further anchoring structure 918 may extend or be joined to a top crown.

Figure 10:
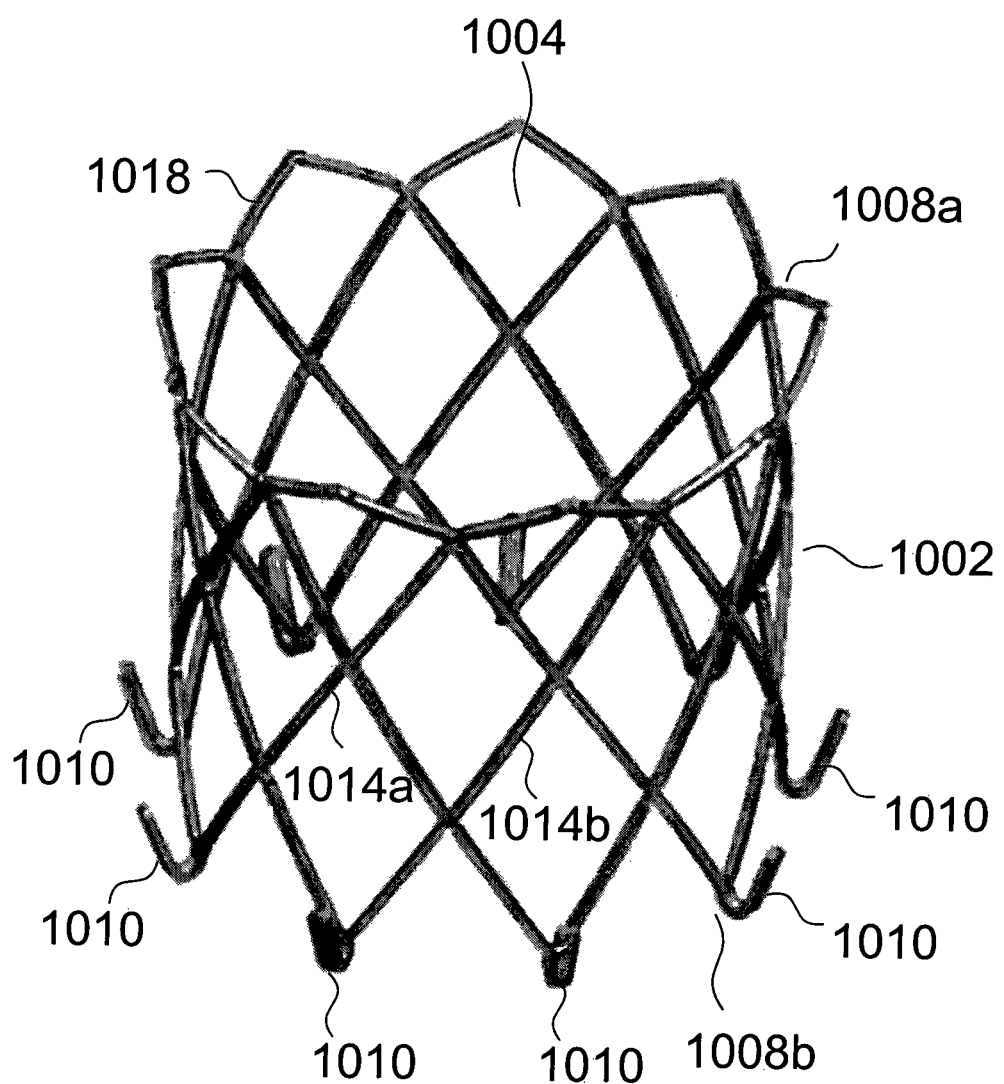
FIG. 10 shows a perspective view of a stent member according to various embodiments.

FIG. 10 shows a perspective view 1000 of a stent member according to various embodiments. The stent member shown in FIG. 10 is in the expanded state. A stent member may include a self-expanding stent frame 1002 defining in its expanded position a central annular opening 1004 along a longitudinal axis. The annular opening may extend from a first end 1008*a* to a second end 1008*b* of the stent frame 1002. The stent member may include a plurality of anchoring structures 1010 extending radially outwards from the second end 1008*b* of the stent frame 1002. The stent member may further include a biocompatible coating on the stent frame 1002.

The stent frame 1002 may include a looped arrangement 1014*a* along a circumference of the stent frame 1002, the looped arrangement 1014*a* including a plurality of stent struts. The stent frame 1002 may also include a further looped arrangement 1014*b* along the circumference of the stent frame 1002, the further looped arrangement 1014*b* including a plurality of further stent struts. The stent struts and plurality of stent struts may form a plurality of top crowns at the first end 1008*a* and a plurality of bottom crowns at the second end 1008*b*.

Each anchoring structure 1010 may include an individual strut or curved hooked structure extending or originating radially outwards and backwards in a direction towards to a plane formed by the first end 1008*a* of the stent member 1002. Each anchoring structure 1018 may extend or be joined to a bottom crown.

The stent member may further include a further anchoring structure 1018 extending radially outwards from the first end 1008*a* of the stent frame 1002. The further anchoring structure may be joined directly to the stent frame 1002, i.e. to the top crowns of the stent frame 1002. The further anchoring structure 1018 may be or may include a skirt member. The further anchoring structure 1018 may include a plurality of struts. For instance, a pair of struts may join neighbouring top crowns. The pair of struts may extend radially outwards from the two neighbouring top crowns and may be joined at a point outside the circumference defined by the stent frame 1002. The pair of struts may also extend away from the plane formed by the second end 1008*b* of the stent frame 1002.

Figure 11:
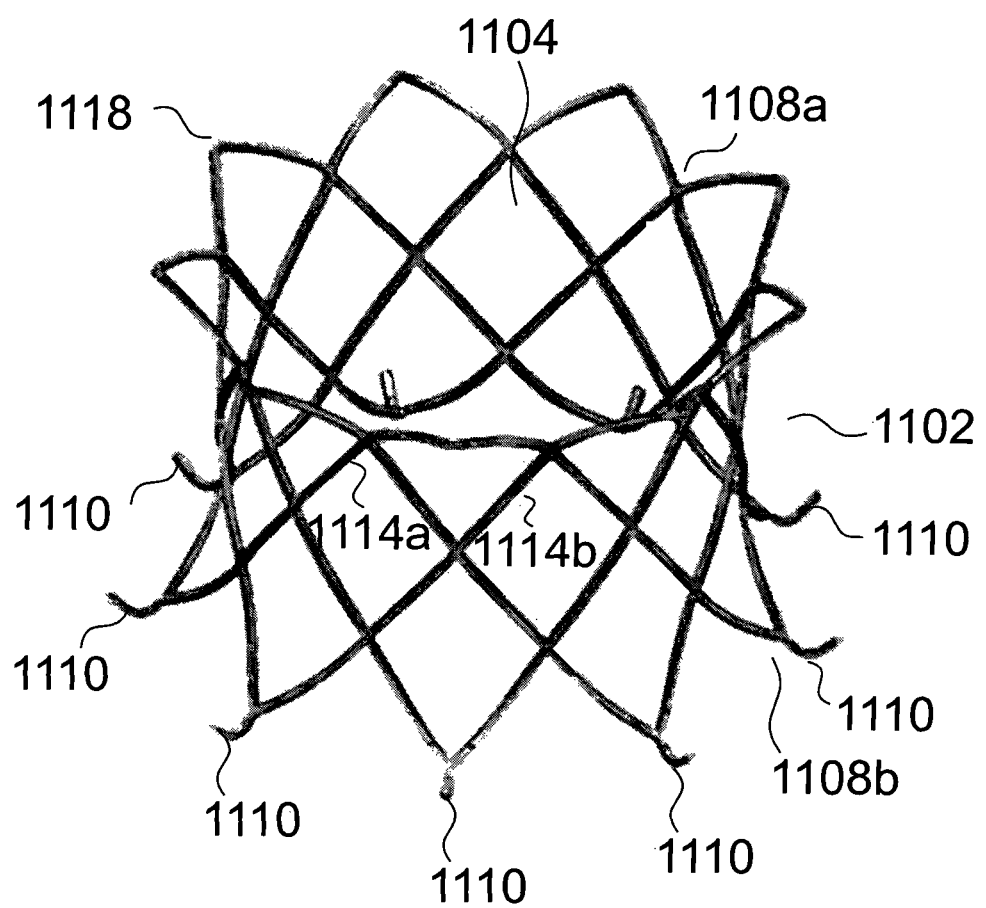
FIG. 11 shows a perspective view of a stent member according to various embodiments.

FIG. 11 shows a perspective view 1100 of a stent member according to various embodiments. The stent member shown in FIG. 11 is in the expanded state. A stent member may include a self-expanding stent frame 1102 defining in its expanded position a central annular opening 1104 along a longitudinal axis. The annular opening may extend from a first end 1108*a* to a second end 1108*b* of the stent frame 1102. The stent member may include a plurality of anchoring structures 1110 extending radially outwards from the second end 1108*b* of the stent frame 1102. The stent member may further include a biocompatible coating on the stent frame 1102.

The stent frame 1102 may include a looped arrangement 1114*a* along a circumference of the stent frame 1102, the looped arrangement 1114*a* including a plurality of stent struts. The stent frame 1102 may also include a further looped arrangement 1114*b* along the circumference of the stent frame 1102, the further looped arrangement 1114*b* including a plurality of further stent struts. The stent struts and plurality of stent struts may form a plurality of top crowns at the first end 1108*a* and a plurality of bottom crowns at the second end 1108*b*. The stent struts and further stent struts may be curved or bent so that the second end 1108*b* of the stent frame 1102 may have a diameter greater than the diameter of the first end 1108*a*. In various alternate embodiments, the second end 1108*b* of the stent frame 1102 may have a diameter smaller or substantially equal to the diameter of the first end 1108*a*.

Each anchoring structure 1110 may include an individual strut or curved hooked structure extending or originating radially outwards and backwards towards to a plane formed by the first end 1108*a* of the stent member 1102. The hooked structure may include a first portion and a second portion extending from the first portion, the first portion substantially perpendicular to a second portion. Each anchoring structure 1118 may extend or be joined to a bottom crown.

The stent member may further include a further anchoring structure 1118 extending radially outwards from the first end 1108a of the stent frame 1102. The further anchoring structure may be joined directly to the stent frame 1102, i.e. to the top crowns of the stent frame 1102. The further anchoring structure 1118 may be or may include a skirt member. The further anchoring structure 1118 may include a plurality of struts. For instance, a pair of struts may join neighbouring top crowns. The pair of struts may extend radially outwards from the two neighbouring top crowns and may be joined at a point outside the circumference defined by the stent frame 1102. The pair of struts may also extend away from the plane formed by the second end 1108b of the stent frame 1102. The pair of struts may join at a point outside the circumference defined by the first end 1108a of the stent frame 1104.

Figure 12:
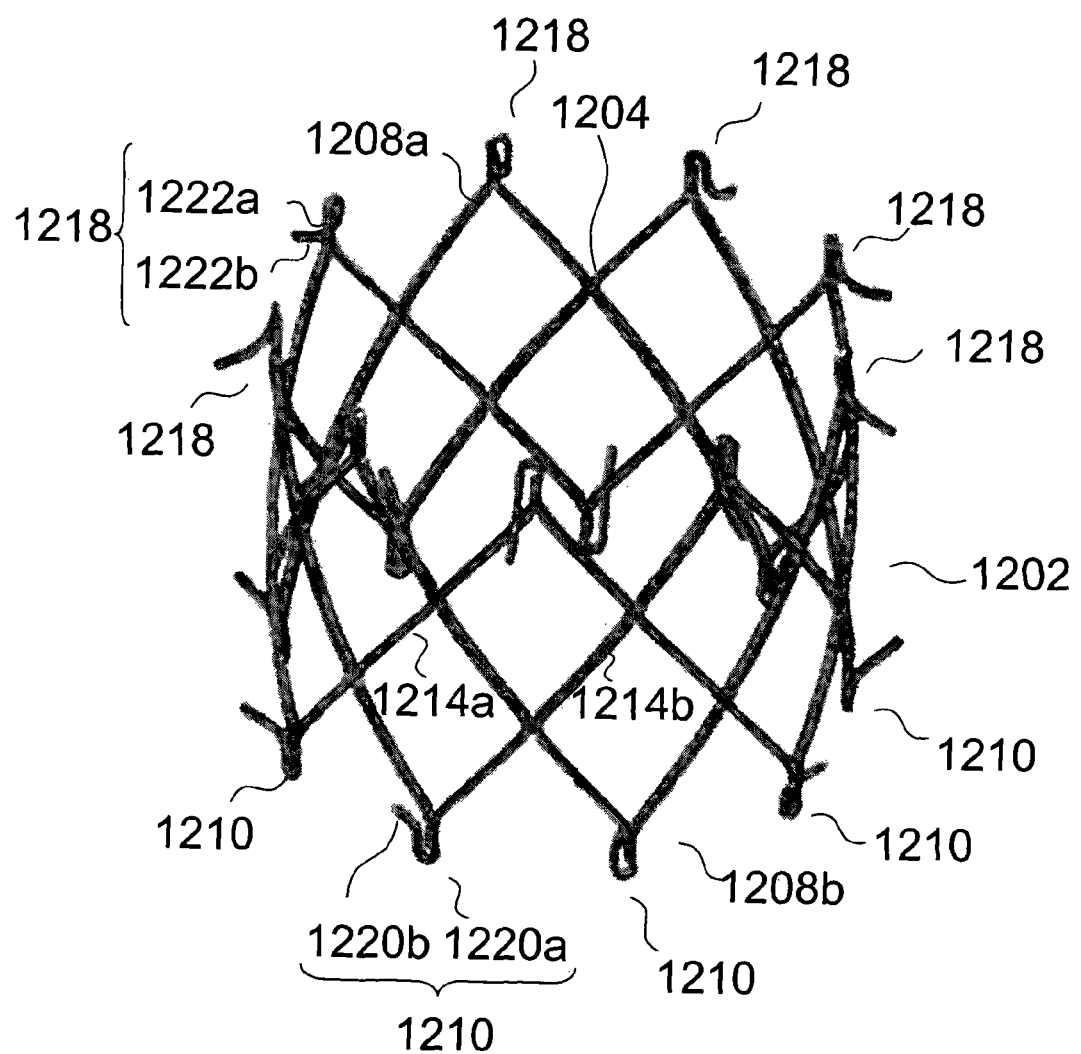
FIG. 12 shows a perspective view of a stent member according to various embodiments.

FIG. 12 shows a perspective view 1200 of a stent member according to various embodiments. The stent member shown in FIG. 12 is in the expanded state. A stent member may include a self-expanding stent frame 1202 defining in its expanded position a central annular opening 1204 along a longitudinal axis. The annular opening may extend from a first end 1208a to a second end 1208b of the stent frame 1202. The stent member may include a plurality of anchoring structures 1210 extending radially outwards from the second end 1208b of the stent frame 1202. The stent member may further include a biocompatible coating on the stent frame 1202.

The stent frame 1202 may include a looped arrangement 1214a along a circumference of the stent frame 1202, the looped arrangement 1214a including a plurality of stent struts. The stent frame 1202 may also include a further looped arrangement 1214b along the circumference of the stent frame 1202, the further looped arrangement 1214b including a plurality of further stent struts. The stent struts and plurality of stent struts may form a plurality of top crowns at the first end 1208a and a plurality of bottom crowns at the second end 1208b. The stent struts and further stent struts may be curved or bent so that the first end 1208a and the second end 1208b may each have a diameter smaller than a diameter defined by a middle portion (between the first end 1208a and the second end 1208b) of the stent frame 1202.

Each anchoring structure 1210 may include a substantially curved portion 1220a and a substantially straight portion 1220b. The substantially curved portion 1220a may extend from or may be joined to the stent frame 1202, i.e. from the bottom crowns of the stent frame 1202. The substantially straight portion 1220b may extend from or may be joined to the substantially curved portion 1220a. The substantially curved portion 1220a may form a loop. The loop may be an enclosed loop or an incomplete loop. The curved portion 1220 may first extend from the second end 1208b in a direction away from the first end 1208a and may subsequently loop radially inwards towards or radially outwards towards the first end 1208a. The substantially straight portion 1220b may extend from the substantially curved portion 1220a radially outwards and towards the first end 1208a.

The stent member may further include a plurality of further anchoring structures 1218 extending radially outwards from the first end 1208a of the stent frame 1202. Each further anchoring structure 1218 may include a substantially curved portion 1222a and a substantially straight portion 1222b. The substantially curved portion 1222a may extend from or may be joined to the stent frame 1202, i.e. from the top crowns of the stent frame 1202. The substantially straight portion 1222b may extend from or may be joined to the substantially curved portion 1222a. The substantially curved portion 1222a may form a loop. The loop may be an enclosed loop or an incomplete loop. The curved portion 1220 may first extend from the first end 1308a in a direction away from the second end 1208b and may subsequently loop radially inwards towards or radially outwards towards the second end 1208b. The substantially straight portion 1222b may extend from the substantially curved portion 1222a radially outwards and towards the second end 1208b.

Figure 13:
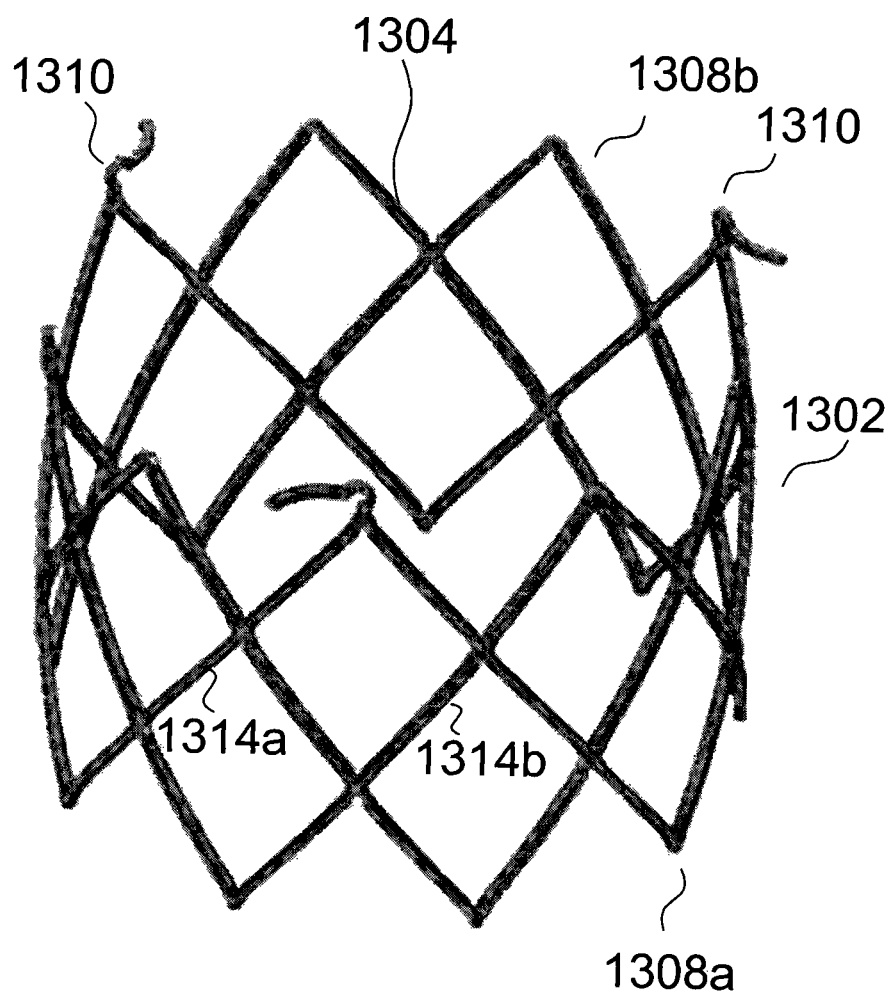
FIG. 13 shows a perspective view of a stent member according to various embodiments.

FIG. 13 shows a perspective view 1300 of a stent member according to various embodiments. The stent member shown in FIG. 13 is in the expanded state. A stent member may include a self-expanding stent frame 1302 defining in its expanded position a central annular opening 1304 along a longitudinal axis. The annular opening may extend from a first end 1308a to a second end 1308b of the stent frame 1302. The stent member may include a plurality of anchoring structures 1310 extending radially outwards from the second end 1308b of the stent frame 1302. The stent member may further include a biocompatible coating on the stent frame 1302.

The stent frame 1302 may include a looped arrangement 1314a along a circumference of the stent frame 1302, the looped arrangement 1314a including a plurality of stent struts. The stent frame 1302 may also include a further looped arrangement 1314b along the circumference of the stent frame 1302, the further looped arrangement 1314b including a plurality of further stent struts. The stent struts and plurality of stent struts may form a plurality of top crowns at the second end 1308b and a plurality of bottom crowns at the first end 1308a. The stent struts and further stent struts may be curved or bent so that the first end 1308a and the second end 1308b may each have a diameter smaller than a diameter defined by a middle portion of the stent frame 1302.

Each anchoring structure 1310 may be or may include a twisted protrusion. An anchoring structure may extend from or may join to only some of the top crowns. For instance, as shown in FIG. 13, the stent frame 1302 may have nine top crowns and an anchoring structure may extend from or may join to only three of the top crowns, i.e. each third top crown may have an anchoring structure 1310 joined to or extending from the top crown.

Figure 14A:
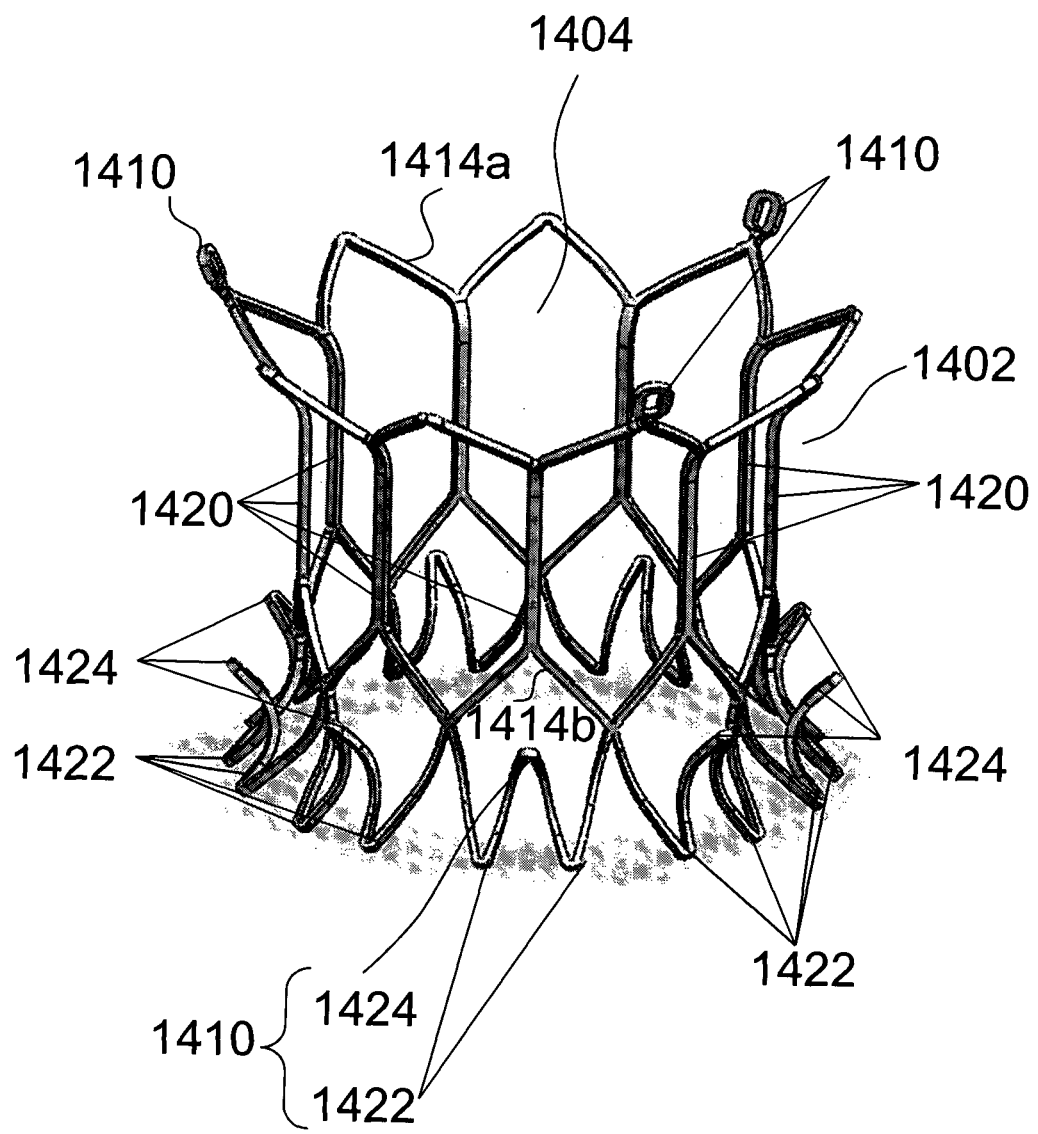
FIG. 14A shows a perspective view of a stent member according to various embodiments.
Figure 14B:
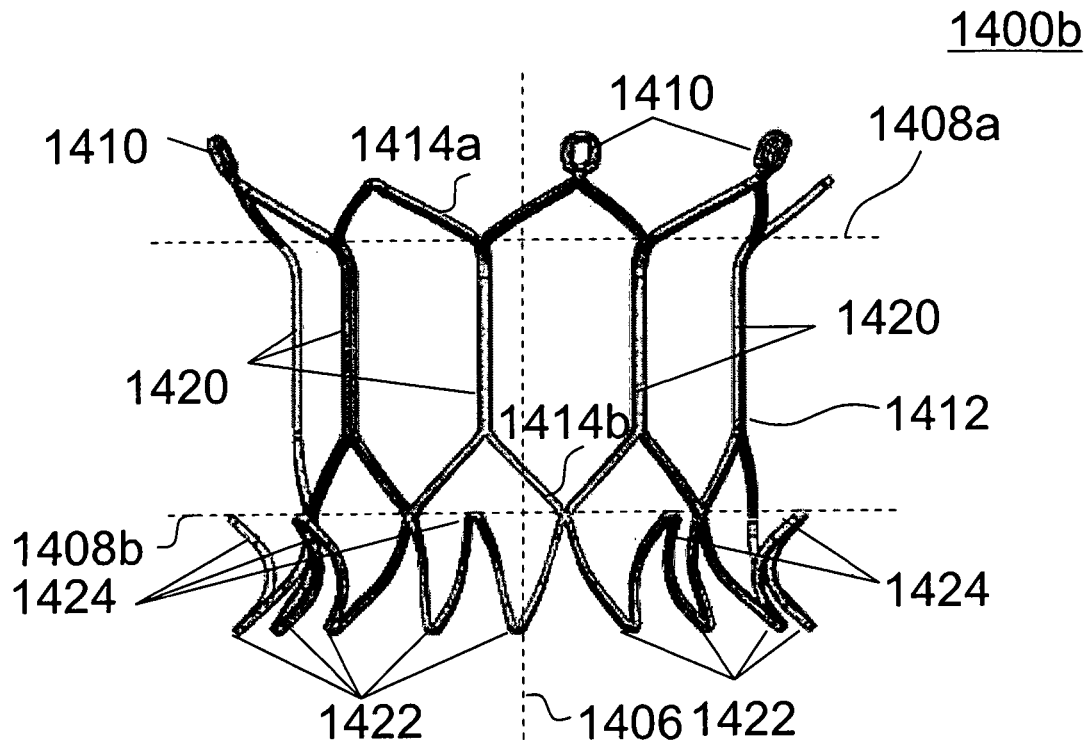
FIG. 14B shows a side view of a stent member similar to the stent member illustrated in FIG. 14A according to various embodiments.
Figure 14C:
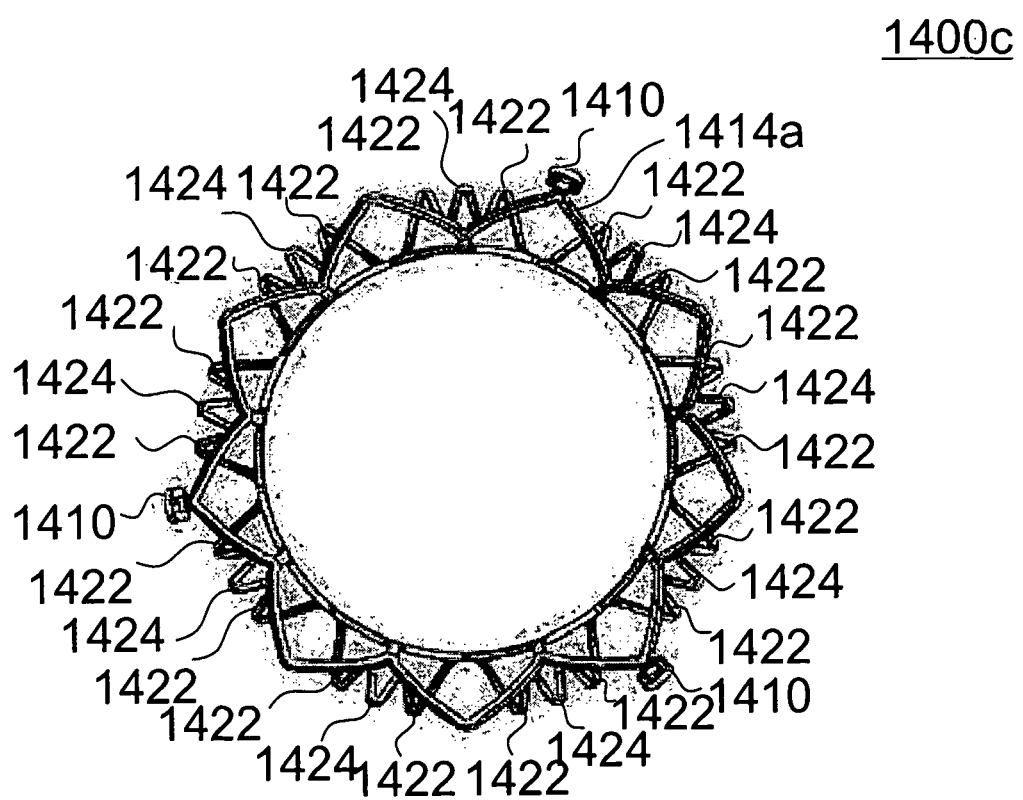
FIG. 14C shows a top view of a stent member similar to the stent member illustrated in FIG. 14A according to various embodiments.

FIG. 14A shows a perspective view 1400a of a stent member according to various embodiments. FIG. 14B shows a side view 1400b of a stent member similar to the stent member illustrated in FIG. 14A according to various embodiments. FIG. 14C shows a top view 1400c of a stent member similar to the stent member illustrated in FIG. 14A according to various embodiments. The stent members shown in FIGS. 14A-C are in the expanded state. A stent member may include a self-expanding stent frame 1402 defining in its expanded position a central annular opening 1404 along a longitudinal axis 1406. The annular opening may extend from a first end 1408a to a second end 1408b of the stent frame 1402. The stent member may include a plurality of anchoring structures 1410 extending radially outwards from the second end 1408b of the stent frame 1402. The stent member may further include a biocompatible coating 1412 on the stent frame 1402.

The stent frame 1402 may include a looped arrangement 1414a along a circumference of the stent frame 1402, the looped arrangement 1414a including a plurality of stent struts. The stent frame 1402 may also include a further looped arrangement 1414b along the circumference of the stent frame, the further looped arrangement 1414b including a plurality of further stent struts. The stent frame 1402 may further include a plurality of axial struts 1420 aligned substantially parallel to the longitudinal axis 1406 of the stent member 1402.

The axial stent struts 1420 may join the looped arrangement 1414a to the looped arrangement 1414b. The axial stent struts 1420 may be bent or curved. In various embodiments, the axial stent struts 1420 may be bent or curved so that the diameter of one end of the stent frame 1402, e.g. the first end 1408a, is greater than the diameter of the other end of the stent frame 1402, e.g. the second end 1408b.

A plurality of top crowns may form the first end 1408a. A plurality of bottom crowns may form the second end 1408b. In various embodiments, the top crowns may extend radially outwards and away from a plane formed by the second end 1408b of the stent frame 1402. The diameter defined by the first end 1408a of the stent frame 1402 may be greater than the diameter defined by the second end 1408b of the stent frame 1402, which may help the device in anchoring and self-aligning as well as helping prevent the device from migrating into the left ventricle post deployment.

A valve member may be attached or sutured on the stent frame 1402.

Each anchoring structure 1410 may be or may include a W-shaped projection. Each anchoring structure 1410 may include two legs 1422 extending from or joined to the second end 1408b, e.g. the bottom crowns. Each anchoring structure 1410 may further include a protruding portion 1424. The protruding tip 1424 may be formed or extended from the legs 1422. The legs 1422 and the protruding tip 1424 may form a W shape. The legs 1422 may extend radially outwards from the second end 1408a and in a direction away from a plane formed by the first end 1408a. The protruding tip 1424 may extend radially outwards from the legs 1422 and away from the plane formed by the second end 1408a. There may be one W-shape projection between two neighbouring bottom crowns. The plurality anchoring structures may be joined together to form a skirt member or skirt frame. In other words, the skirt member or skirt frame may include the plurality of W-shaped projections. The skirt member or skirt frame may include stent struts extending radially outwards and downwards to form legs 1422 as well as stent struts extending radially outwards and upwards to form tip 1424.

The skirt member or skirt frame may provide anchoring as well as to provide sealing. The skirt member or skirt frame may be coated with a biocompatible material for reducing paravalvular leakages around the device post deployment. The plurality of anchoring structures 1410 may be designed to latch onto the chordae tendinae of the native mitral valve leaflet in the ventricular space, which helps to anchor the device and prevent migration into the atrium during ventricular systole. The struts arranged in a W-shaped manner may also facilitate packing, crimping and loading onto a delivery, system, such as a catheter, for deployment.

The stent member may further include a plurality of further anchoring structures 1410 extending radially outwards from the first end 1408a of the stent frame 1402. Each further anchoring structure 1410 may be a ring. The further anchoring structures 1410 may also help to anchor the device and prevent the device from migrating into the left ventricle post deployment.

Figure 14D:
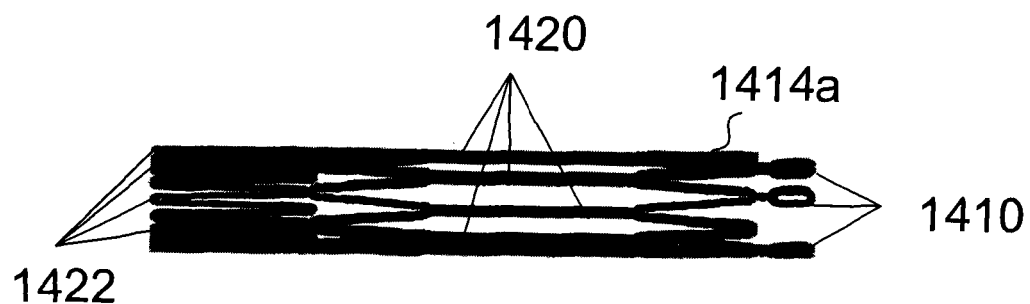
FIG. 14D shows a perspective view of a stent member similar to the stent member illustrated in FIG. 14A in a collapsed state according to various embodiments.

FIG. 14D shows a perspective view 1400d of a stent member similar to the stent member illustrated in FIG. 14A in a collapsed state according to various embodiments. The legs 1422 and the protruding portion 1424 may be aligned parallel to the longitudinal axis 1406 when the stent member is in the collapsed state. The diameter of the stent frame 1402 when the stent member is in the collapsed state may be smaller than the diameter of the stent frame when the stent member is in the expanded state. The stent member may be configured to be deployed by a catheter in the human or animal body when the stent member is in the collapsed state.

Figure 14E:
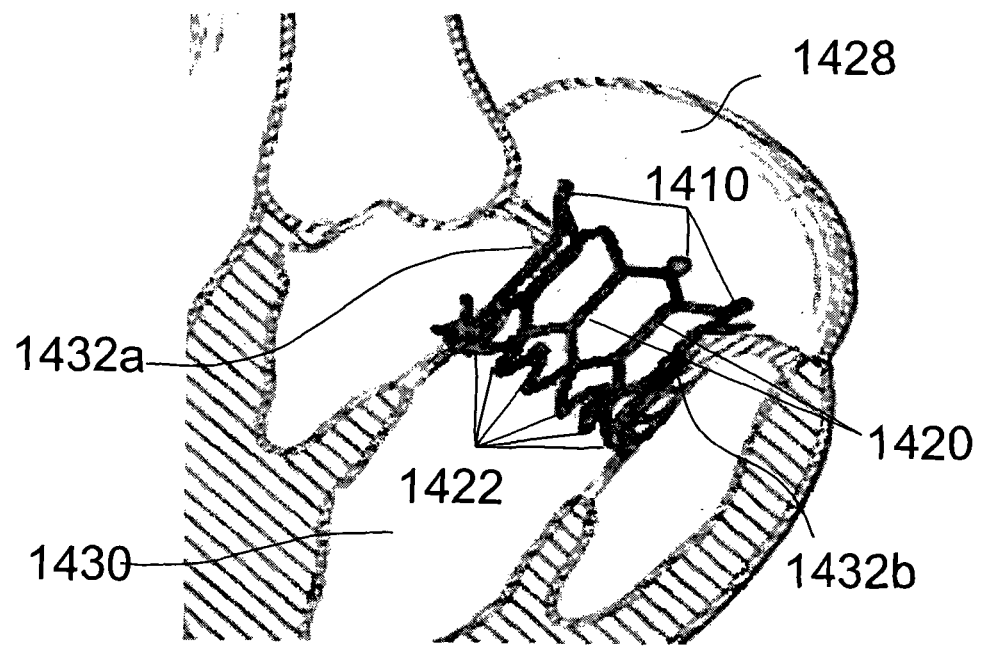
FIG. 14E shows a side view of a stent member similar to the stent member illustrated in FIG. 14A according to various embodiments being deployed as part of a percutaneous mitral valve replacement device in the heart.

FIG. 14E shows a side view 1400e of a stent member similar to the stent member illustrated in FIG. 14A according to various embodiments being deployed as part of a percutaneous mitral valve replacement device in the heart. The percutaneous mitral valve replacement device may further include a valve member (not shown in FIG. 14E) attached or sutured to the stent member. The stent member may be positioned between the left atrium 1428 and the left ventricle 1430. The self-expanding stent frame 1402 may push against the leaflets of the biological mitral valve. The anchoring structures 1410 may anchor to the leaflets of the mitral valve by clamping the tips of the leaflets. The further anchoring structures may anchor on the upper portions of the mitral valve or atrial tissues.

The stent frame 1402 may have a central tubular portion that has a substantially uniform diameter. The stent frame 1402 may be sufficiently long enough to ensure that the valve member may be attached or sutured to the substantially cylindrical portion of the stent member for optimal performance and durability of the valve member. The absence of cross diamond struts in the tubular portion of the stent member may reduce radial force of the stent member thereby enhancing the conforming ability of the device to the D-shaped annulus of the native mitral valve.

Different features of the different various embodiments described herein may be combined as appropriate. For example, the further anchoring structures 1410 in FIG. 14A may additionally or alternatively used in stent members according to various embodiments shown in FIG. 9.

FIG. 15 is a schematic 1500 illustrating a method of implanting an artificial valve. The method may include, in 1502, inserting the artificial valve using a valve delivery system, the stent member in a collapsed state. The artificial valve may be any artificial valve described herein. The stent member may be configured to self-expand to an expanded state upon release by the valve delivery system. When the stent member expands, the artificial valve may be implanted, for instance between the left atrium and left ventricle of the heart. The valve delivery system may be a catheter.

The method may also include crimping or bending the artificial valve into a collapsed state before insertion. The method may further include hooking the anchoring structure and/or further anchoring structures of the stent member to a release mechanism prior to implantation/insertion. The method may further include using the release mechanism to release the anchoring structure and/or further anchoring structures for securing the artificial valve to biological tissues during implantation. Prior to releasing the release mechanism, the artificial valve may still be re-positionable and retrievable.

Implantation of the artificial valve may be guided by Fluorsoscopy and/or Transesophageal Echocardiography. The artificial valve may be inserted through the jugular vein, and may be transseptally delivered to the diseased mitral valve. Both longitudinal and cross-sectional views of the left heart chambers may allow for the detailed imaging of the mitral valve including the annulus (ring) as well as blood flow dynamics to and from the mitral valve. The effects of the deployment may be monitored in real-time fashion.

At present, patients suffering from mitral regurgitation may have the options of deciding either for open heart valve replacement or for percutaneous mitral valve repairs depending on the quality of the valve tissue and the expertise of surgeon. The former may entail the risks of surgery-related complications that could compromise the recovery and survival rates of the patients. Such risks may be compounded by factors such as advanced age of patients, redo procedures and comorbidities. Although the latter may provide better survival rates, percutaneous mitral valve repairs may entail a more complicated and protracted surgical procedure.

Percutaneous mitral valve replacement procedure may combine the advantages of open heart valve replacement and percutaneous mitral valve repairs. Percutaneous mitral valve replacement may include minimally invasive delivery of an artificial valve through a catheter to replace a degenerative mitral valve without incurring the risks of open chest surgery. As demonstrated in animal trials, the deployment of the artificial valve may take approximately 15-20 s. In addition, the procedure may not require severing the mitral chord and as a result may help maintain the physiological geometry of the mitral annulus and preservation of postoperative ejection fraction (EF).

Transcatheter valves represent an attractive market opportunity as the technology may potentially expand the overall heart valve market and convert higher risk patients to a less invasive approach. Various embodiments may be relevant to the cardiovascular devices industry, which in recent years has emerged as the largest and fastest growing markets in the medical equipment industry with one of the key thrusts being the cardiovascular prosthetic devices. Cardiovascular prosthetic devices for less invasive mitral valve repair may have an approximated market size of US$2 billion. American Heart Association statistics see a trend of significant increase in percutaneous coronary interventions Major companies involved in development of cardiovascular device include Edward LifeSciences, Medtronics, Sulzer Carbomedics and St Jude Medical.

Edward LifeSciences's market share of transcatheter valves is projected to exceed US$1.2 billion in 2014 while Johnson and Johnson (J&J)'s market share is projected to be US$750-800 millions in 2012. Medtronic's share of transcatheters is expected to reach US$1.5 billion in 2014.

Percutaneous valve intervention technique has been received with enthusiasm by professionals and commercial companies for the past years. Early clinical experiences with percutaneous aortic valve replacements together with the limited pre-clinical experiments with percutaneous mitral valves show the feasibility of the technique with favorable outcomes. The limitations of the technology relates to surgical procedures, which may have a steep learning curve and which may require an intimate and fundamental knowledge of the anatomy and physiology of the failing heart valves.

The obstacles faced by percutaneous mitral valve replacement surgery may include the lack of adequate echocardiographic visualization or fluoroscopic landmarks of the mitral valve apparatus necessary for the accurate deployment of the stent. The second impediment may be the obstruction to the left ventricular outflow tract (LVOT), due to of the anchoring of the artificial valve inside the mitral valve annulus using radial forces. The third problem relates to the anatomy of the biological mitral valve apparatus, particularly the chordae tendineae, which may impede the complete expansion, accurate positioning, and/or anchorage of the artificial valve. Further, there is a challenge to ensure that severe mitral valve stenosis by microemboli of calcified material have to be prevented. However, such problems have not posed a prohibitive limitation for aortic valve replacement through the percutaneous route. Obstacles may be resolved with adequate number of properly planned animal experiments, which may help fine-tune many of the surgical procedures. In the case of the microemboli, trans-cranial Doppler may help detect embolic activity while the procedure is carried out and in the rare case of such events, a meshwork-net may be inserted into the aorta for the few seconds of deployment to catch any disengaging debris which could obstruct brain arteries.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A stent member comprising:
 a self-expanding stent frame defining in its expanded position a central annular opening along a longitudinal axis, the opening extending from a first end to a second end of the stent frame;
 at least one anchoring structure extending radially outwards from the second end of the stent frame;
 a plurality of further anchoring structures extending radially outwards from the first end of the stent frame; and
 a biocompatible coating on the stent frame;
 wherein each further anchoring structure comprises an elongated member extending radially outwards and backwards towards to a plane formed by the second end of the stent frame;
 wherein each further anchoring structure further comprises a hook member, the hook member having a first elongate portion and a second elongate portion;
 wherein the first elongate portion extends backwards from the first end of the stent frame towards the plane formed by the second end; and
 wherein the second elongate portion extends from the first elongate portion outwards away from the stent frame.

2. The stent member according to claim 1,
 wherein the stent frame comprises a looped arrangement along a circumference of the stent frame, the looped arrangement comprising a plurality of stent struts, each stent strut having a first end joined to a first neighbouring stent strut and a second end joined to a second neighbouring stent strut.

3. The stent member according to claim 2,
 wherein each stent strut is joined to the first neighbouring stent strut at a first acute angle, and wherein each stent strut is joined to the second neighbouring stent strut at a second acute angle.

4. The stent member according to claim 2,
 wherein the stent frame comprises a further looped arrangement along the circumference of the stent frame, the further looped arrangement comprising a plurality of further stent struts, each further stent strut having a first end joined to a further first neighbouring stent strut and a second end joined to a further second neighbouring stent strut; and
 wherein the stent struts of the looped arrangement are joined to the further stent struts of the further looped arrangement to form a plurality of cells.

5. The stent member according to claim 4,
wherein the cells are in multiples of three.

6. The stent member according to claim 5,
wherein the stent member comprises at least three cells.

7. The stent member according to claim 4,
wherein the stent frame further comprises axial struts aligned substantially parallel to the longitudinal axis of the stent member; and
wherein the stent struts of the looped arrangement are joined to the further stent struts of the further looped arrangement via the axial struts to form the plurality of cells.

8. The stent member according to claim 1,
wherein the at least one anchoring structure comprises a plurality of anchoring structures extending radially outwards from the second end of the stent frame; and
wherein each anchoring structure comprises an elongated member extending radially outwards.

9. The stent member according to claim 8,
wherein each anchoring structure further comprises a plurality of protrusions extending from the elongated member.

10. The stent member according to claim 1,
wherein the at least one anchoring structure is a skirting frame; and wherein an outer diameter of the skirting frame is greater than an outer diameter of the stent frame.

11. The stent member according to claim 1,
wherein the stent frame further comprises anchoring protrusions extending from the stent frame.

12. The stent member according to claim 1,
wherein the stent member is collapsible.

13. The stent member according to claim 1,
wherein the stent frame is a nitinol frame.

14. An artificial valve comprising:
a stent member; and
a valve member attached to the stent member;
wherein the stent member comprises:
    a self-expanding stent frame defining in its expanded position a central annular opening along a longitudinal axis, the opening extending from a first end to a second end of the stent frame;
    at least one anchoring structure extending radially outwards from the second end of the stent frame;
    a plurality of further anchoring structures extending radially outwards from the first end of the stent frame; and
    a biocompatible coating on the stent frame;
    wherein each further anchoring structure comprises an elongated member extending radially outwards and backwards towards to a plane formed by the second end of the stent frame;
    wherein each further anchoring structure further comprises a hook member, the hook member having a first elongate portion and a second elongate portion;
    wherein the first elongate portion extends backwards from the first end of the stent frame towards the plane formed by the second end; and
    wherein the second elongate portion extends from the first elongate portion outwards away from the stent frame.

15. A method of implanting an artificial valve, the method comprising:
inserting the artificial valve using a valve delivery system, the artificial valve comprising a stent member and a valve member attached to the stent member, the stent member in a collapsed state;
wherein the stent member is configured to self-expand to an expanded state upon release by the valve delivery system;
wherein the stent member comprises:
    a self-expanding stent frame defining in its expanded position a central annular opening along a longitudinal axis, the opening extending from a first end to a second end of the stent frame;
    at least one anchoring structure extending radially outwards from the second end of the stent frame;
    a plurality of further anchoring structures extending radially outwards from the first end of the stent frame; and
    a biocompatible coating on the stent frame;
    wherein each further anchoring structure comprises an elongated member extending radially outwards and backwards towards to a plane formed by the second end of the stent frame;
    wherein each further anchoring structure further comprises a hook member, the hook member having a first elongate portion and a second elongate portion;
    wherein the first elongate portion extends backwards from the first end of the stent frame towards the plane formed by the second end; and
    wherein the second elongate portion extends from the first elongate portion outwards away from the stent frame.

* * * * *